US008435943B2

(12) United States Patent
Garigapati et al.

(10) Patent No.: US 8,435,943 B2
(45) Date of Patent: *May 7, 2013

(54) PROTEIN STABILIZATION FORMULATIONS

(75) Inventors: Venkata R. Garigapati, Southborough, MA (US); Dongling Su, Franklin, MA (US); Rehan Khanzada, Middleborough, MA (US); Steven J. Sawamura, Newark, CA (US)

(73) Assignee: Advanced Technogies and Regenerative Medicine, LLC, Raynham, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 13/089,683

(22) Filed: Apr. 19, 2011

(65) Prior Publication Data

US 2011/0237506 A1    Sep. 29, 2011

Related U.S. Application Data

(62) Division of application No. 11/950,127, filed on Dec. 4, 2007, now Pat. No. 7,956, 028.

(60) Provisional application No. 60/870,032, filed on Dec. 14, 2006.

(51) Int. Cl.
*A61K 38/00* (2006.01)
*A61K 38/16* (2006.01)
*A61K 38/17* (2006.01)
*A61K 38/18* (2006.01)

(52) U.S. Cl.
USPC ............ 514/7.6; 514/8.8; 514/8.9; 514/16.7; 514/16.8; 514/16.9; 514/17.1; 514/17.2; 424/422; 424/423

(58) Field of Classification Search .................. None
See application file for complete search history.

(56) References Cited

U.S. PATENT DOCUMENTS

| | | | |
|---|---|---|---|
| 2,931,802 A | 4/1960 | Touey |
| 4,120,810 A | 10/1978 | Palmer |
| 4,891,319 A | 1/1990 | Roser |
| 5,011,691 A | 4/1991 | Oppermann |
| 5,013,649 A | 5/1991 | Wang |
| 5,202,311 A | 4/1993 | Folkman |
| 5,231,169 A | 7/1993 | Constantz |
| 5,266,683 A | 11/1993 | Oppermann |
| 5,318,898 A | 6/1994 | Israel |
| 5,385,887 A | 1/1995 | Yim |
| 5,411,941 A | 5/1995 | Grinna |
| 5,455,231 A | 10/1995 | Constantz |
| 5,516,654 A | 5/1996 | Israel |
| 5,658,882 A | 8/1997 | Celeste |
| 5,747,058 A | 5/1998 | Tipton |
| 5,770,700 A | 6/1998 | Webb |
| 5,776,193 A | 7/1998 | Kwan |
| 5,801,014 A | 9/1998 | Lee |
| 5,804,557 A | 9/1998 | Cleland |
| 5,866,165 A | 2/1999 | Liu |
| 5,955,448 A | 9/1999 | Colaco |
| 5,972,385 A | 10/1999 | Liu |
| 5,985,320 A | 11/1999 | Edwards |
| 6,051,558 A | 4/2000 | Burns |
| 6,071,428 A | 6/2000 | Franks |
| 6,165,981 A | 12/2000 | Flaa |
| 6,171,584 B1 | 1/2001 | Hötten |
| 6,171,586 B1 | 1/2001 | Lam |
| 6,187,742 B1 | 2/2001 | Wozney |
| 6,207,718 B1 | 3/2001 | Papadimitriou |
| 6,281,195 B1 | 8/2001 | Rueger |
| 6,284,872 B1 | 9/2001 | Celeste |
| 6,288,043 B1 | 9/2001 | Spiro |
| 6,340,369 B1 | 1/2002 | Ferree |
| 6,344,058 B1 | 2/2002 | Ferree |
| 6,352,557 B1 | 3/2002 | Ferree |
| 6,407,060 B1 | 6/2002 | Charette |
| 6,419,702 B1 | 7/2002 | Ferree |
| 6,454,804 B1 | 9/2002 | Ferree |
| 6,551,801 B1 | 4/2003 | Andou |
| 6,645,247 B2 | 11/2003 | Ferree |
| 6,648,918 B2 | 11/2003 | Ferree |
| 6,648,919 B2 | 11/2003 | Ferree |
| 6,648,920 B2 | 11/2003 | Ferree |
| 6,656,492 B2 | 12/2003 | Kajiyama |
| RE38,385 E | 1/2004 | Franks |
| 6,685,695 B2 | 2/2004 | Ferree |

(Continued)

FOREIGN PATENT DOCUMENTS

| | | |
|---|---|---|
| EP | 0621044 | 10/1994 |
| EP | 0955313 A1 | 11/1999 |

(Continued)

OTHER PUBLICATIONS

Letter from Keith E. Gilman of Lerner David Littenberg Krumholz & Mentlik LLP, dated Sep. 13, 2010 regarding Johnson & Johnson U.S. Publication No. 2008/0147077A1.
EP Search Report for App No. PCT/US2009/039925 dated Aug. 10, 2009.
European Search Report for Application No. 07254571.8, dated May 8, 2008.
PCT Search Report dated Jul. 10, 2008 for application No. PCT/US2008/068007.
Gupta, Lectin anchored stabilized biodegradable nanoparticles for oral immunization, International Journal of Pharmaceutics, 318 (2006) 163-173.
Von Heijne, A new method for predicting signal sequence cleavage sites, Nucleic Acids Research, 14:4683-4691 (1986).
Dayhoffel et al., A Model of Evolutionary Change in Proteins, Atlas of Protein Sequence and Structure, vol. Suppl 3., pp. 354-352 1978.
Rickert et al., A Growth and Differentiation Factor-5 (GDF-5)-coated Suture Stimulates Tendon healing in an Achilles Tendon Model in Rats, Growth Factors, vol. 19, 2001, 115-126.
Schmidmaier, G, et al., Biodegradable Poly(D,L-Lactide) Coating of Implants for Continuous Release of Growth Factors, Biomedical Materials Res Appl Biomat, 58, 449-455, 2001.

*Primary Examiner* — Elizabeth C Kemmerer

(57) ABSTRACT

The present invention is directed to stabilizing Bone Morphogenetic Protein in various lyophilized formulations and compositions. The present invention comprises formulations primarily including trehalose as an excipient for lyophilized compositions and their subsequent storage and reconstitution, and can also optionally include other excipients, including buffers and surfactants.

5 Claims, 10 Drawing Sheets

U.S. PATENT DOCUMENTS

| | | |
|---|---|---|
| 6,719,968 B2 | 4/2004 | Celeste |
| 6,723,170 B2 | 4/2004 | Ohashi |
| 6,755,863 B2 | 6/2004 | Ferree |
| 6,764,994 B1 | 7/2004 | Hötten |
| 6,780,324 B2 | 8/2004 | Le Garrec |
| 6,911,411 B2 | 6/2005 | Cox |
| 6,936,582 B1 | 8/2005 | Charette |
| 6,991,790 B1 | 1/2006 | Lam |
| 6,992,065 B2 | 1/2006 | Okumu |
| 7,060,268 B2 | 6/2006 | Andya |
| RE39,497 E | 2/2007 | Franks |
| 7,235,527 B2 | 6/2007 | Makishima |
| 7,318,840 B2 | 1/2008 | McKay |
| 7,323,445 B2 | 1/2008 | Zhang |
| 7,375,077 B2 | 5/2008 | Mao |
| 7,435,260 B2 | 10/2008 | Ferree |
| 7,572,440 B2 | 8/2009 | Vukicevic |
| 7,678,764 B2 | 3/2010 | Garigapati |
| 7,956,028 B2 * | 6/2011 | Garigapati et al. ............ 514/7.6 |
| 2001/0024823 A1 | 9/2001 | Vukicevic et al. |
| 2002/0032155 A1 | 3/2002 | Ferree |
| 2002/0064516 A1 | 5/2002 | Arvine et al. |
| 2002/0128718 A1 | 9/2002 | Ferree |
| 2002/0165542 A1 | 11/2002 | Ferree |
| 2002/0173770 A1 | 11/2002 | Flory |
| 2003/0026788 A1 | 2/2003 | Ferree |
| 2003/0185812 A1 | 10/2003 | Ferree |
| 2003/0192554 A1 | 10/2003 | Ferree |
| 2004/0022771 A1 | 2/2004 | Ferree |
| 2004/0024471 A1 | 2/2004 | Ferree |
| 2004/0028733 A1 | 2/2004 | Tracy |
| 2004/0132653 A1 | 7/2004 | Ichikawa |
| 2004/0146923 A1 | 7/2004 | Celeste |
| 2004/0197324 A1 | 10/2004 | Liu |
| 2005/0069571 A1 | 3/2005 | Slivka |
| 2005/0119754 A1 | 6/2005 | Trieu |
| 2005/0191248 A1 | 9/2005 | Hunter |
| 2006/0024346 A1 | 2/2006 | Brody |
| 2006/0088565 A1 | 4/2006 | Kohnert |
| 2006/0121113 A1 | 6/2006 | Bartholomaeus |
| 2006/0223120 A1 | 10/2006 | Kim |
| 2006/0286171 A1 | 12/2006 | Zhou |
| 2006/0286289 A1 | 12/2006 | Prajapati |
| 2006/0287676 A1 | 12/2006 | Prajapati |
| 2007/0020255 A1 | 1/2007 | Ueno et al. |
| 2007/0053871 A1 | 3/2007 | Li |
| 2007/0098756 A1 | 5/2007 | Behnam |
| 2007/0172479 A1 | 7/2007 | Warne |
| 2007/0178159 A1 | 8/2007 | Chen |
| 2008/0098614 A1 | 5/2008 | Tchessalov |
| 2008/0147077 A1 | 6/2008 | Garigapati |
| 2008/0234727 A1 | 9/2008 | Garigapati |
| 2008/0311078 A1 | 12/2008 | Gokarn |
| 2009/0004048 A1 | 1/2009 | Elliott |
| 2009/0030483 A1 | 1/2009 | Risi |
| 2009/0043078 A1 | 2/2009 | Daniel |
| 2009/0048412 A1 | 2/2009 | Soula |
| 2009/0060976 A1 | 3/2009 | Rueger |
| 2009/0099089 A1 | 4/2009 | Zhang |
| 2009/0259023 A1 | 10/2009 | Su |
| 2009/0286764 A1 | 11/2009 | Kipp |
| 2009/0291062 A1 | 11/2009 | Fraunhofer |
| 2010/0015230 A1 | 1/2010 | Ron |
| 2010/0041870 A1 | 2/2010 | Tchessalov |
| 2010/0130730 A1 | 5/2010 | Garigapati |
| 2010/0144631 A1 | 6/2010 | Ron |
| 2010/0255100 A1 | 10/2010 | Margolin |

FOREIGN PATENT DOCUMENTS

| | | |
|---|---|---|
| EP | 957943 B1 | 5/2003 |
| EP | 1314437 | 5/2003 |
| EP | 1350525 A2 | 10/2003 |
| EP | 1448246 | 8/2004 |
| EP | 1462126 A1 | 9/2004 |
| EP | 1274459 B1 | 11/2005 |
| EP | 1604693 | 12/2005 |
| EP | 1604963 A2 | 12/2005 |
| EP | 0955313 B1 | 5/2006 |
| EP | 1698640 | 9/2006 |
| EP | 1915986 A1 | 4/2008 |
| EP | 1932519 A1 | 6/2008 |
| EP | 957943 B2 | 11/2008 |
| GB | 2164042 | 3/1986 |
| JP | 60253455 | 12/1985 |
| JP | 62135431 | 6/1987 |
| JP | 6-305983 | 11/1994 |
| JP | 2004529917 | 9/2004 |
| JP | 2005527503 | 9/2005 |
| WO | WO 8800205 A1 | 1/1988 |
| WO | WO 9011366 A1 | 10/1990 |
| WO | WO 9118098 A1 | 11/1991 |
| WO | WO 9200382 A1 | 1/1992 |
| WO | WO 9309229 A1 | 5/1993 |
| WO | WO 9316099 A2 | 8/1993 |
| WO | WO 9410203 A2 | 5/1994 |
| WO | WO 9415949 A1 | 7/1994 |
| WO | WO 9415965 A1 | 7/1994 |
| WO | WO 9415966 A1 | 7/1994 |
| WO | WO 9421681 A1 | 9/1994 |
| WO | WO 9426892 A1 | 11/1994 |
| WO | WO 9426893 A1 | 11/1994 |
| WO | WO 9501801 A1 | 1/1995 |
| WO | WO 95/04819 A1 | 2/1995 |
| WO | WO 9510539 A1 | 4/1995 |
| WO | WO 9510802 A1 | 4/1995 |
| WO | WO 9516035 A2 | 6/1995 |
| WO | WO 9533830 A1 | 12/1995 |
| WO | WO 9601316 A1 | 1/1996 |
| WO | WO 9601845 A1 | 1/1996 |
| WO | WO 96/14335 A1 | 5/1996 |
| WO | WO 9636710 A1 | 11/1996 |
| WO | WO 0178683 A2 | 10/2001 |
| WO | WO 0213860 | 2/2002 |
| WO | WO 02/066096 A2 | 8/2002 |
| WO | WO 02080976 | 10/2002 |
| WO | WO 03000282 A1 | 1/2003 |
| WO | WO 03030923 A1 | 4/2003 |
| WO | WO 03/043673 | 5/2003 |
| WO | WO 2003066120 A1 | 8/2003 |
| WO | WO 03072060 | 9/2003 |
| WO | WO 2004037265 A1 | 5/2004 |
| WO | WO 2004052336 A2 | 6/2004 |
| WO | WO 200533143 | 4/2005 |
| WO | WO 2005060989 A1 | 7/2005 |
| WO | WO 2005100399 A2 | 10/2005 |
| WO | WO 2005107765 A2 | 11/2005 |
| WO | WO 2005115438 A1 | 12/2005 |
| WO | WO 2006138099 A2 | 12/2006 |
| WO | WO 2006138181 | 12/2006 |
| WO | WO 2007025441 A1 | 3/2007 |
| WO | WO 2008009419 A1 | 1/2008 |
| WO | WO 2008045498 A1 | 4/2008 |
| WO | WO 2008049588 A1 | 5/2008 |
| WO | WO 2008079672 A2 | 7/2008 |
| WO | WO 2008082563 A2 | 7/2008 |
| WO | WO 2008/099198 A2 | 8/2008 |
| WO | WO 2008099190 A2 | 8/2008 |
| WO | WO 2008143867 A1 | 11/2008 |
| WO | WO 2009006097 A1 | 1/2009 |
| WO | WO 2009006301 A2 | 1/2009 |
| WO | WO 2009015736 A1 | 2/2009 |
| WO | WO 2009016131 A1 | 2/2009 |
| WO | WO 2009016333 A1 | 2/2009 |
| WO | WO 2009020744 A1 | 2/2009 |

OTHER PUBLICATIONS

Rothenberger, In Vitro Antimicrobial Evaluation of Coated VICRYL* Plus Antibacterial Suture (Coated Polyglactin 910 with Triclosan) using Zone of Inhibition Assays, Surgical Infection Society Journal Supp, Dec. 2002, p. S79-87.

Mangram, Guideline for Prevention of Surgical Site Infection, Infection Control and Hospital Epidemiology, 1999, vol. 20, No. 4, 250-278).

Wozney et al., Novel Regulators of Bone Formation: Molecular Clones and Activities, Science 242:1528-1534, 1988.

Padgett et al., A transcript from a *Drosophila* pattern gene predicts a protein homologous to the transforming growth factor-B family, Nature 325:81-84 (1987).

Needleman et al., A General Method Applicable to the Search for Similarities in the Amino Acid Sequence of Two Proteins, J. Mol. Biol. 48:443-453 (1970).

Lee et al., Expression of growth/differentiation factor 1 in the nervous system: Conservation of a bicistronic structure, Proc. Natl. Acad. Sci 88:4250-4254, 1991.

Storm et al., Limb alterations in brachypodism mice due to mutations in a new member of the TGFβ-superfamily, Nature 368:639-643 1994.

Takao et al., Identification of Rate Bone Morphogenetic Protein-3b (BMP-3b), a New Member of BMP-3, Biochemical and Biophysical Research Communications, 219:656-662, 1996.

Basler et al., Control of Cell Pattern in the Neural Tube: Regulation of Cell Differentiation by dorsalin-1, a Novel TGFβ Family Member, Cell 73:687-702, 1993.

Mazzocca, Tendon and Bone Cell Reponses to a Novel Suture Material, American Academy of Orthopedic Surgeons, Abstract #338 2005.

Wright, Meniscal Healing Using Butyric Acid Impregnated Sutures, 50th Annual Meeting of the Orthopedic Research Society, #1234 2004.

Peterson, et al., The Effect of Locally Vascular Endothelial Growth Factor on Meniscus Healing, $51^{st}$ Annual Meeting of the Orthopedic Research Society, No. 0076, 2007.

Weeks, A Maternal mRNA Localized to the Vegetal Hemisphere in Zenopus Eggs Codes for a Growth Factor Related to TGF-β, Cell, Vo. 51, 861-867, 1987.

Arakawa et al., Factors affecting short-term and long-term stabilities of protein, Advanced Drug Delivery Reviews, 2001, pp. 307-326, vol. 46.

Celeste, AJ et. al., "Identification of Transforming Growth Factor Beta Family Members Present in Bone-Inductive Protein Purified from Bovine Bone", Proceedings of the National Academy of Science, 1990, pp. 9843-9847, vol. 87, Issue 24.

Crowe, J., "The Trehalose Myth Revisited: Introduction to a Symposium on Stabilization of Cells in the Dry State", Cryobiology, Sep. 2001, pp. 89-105, vol. 43, Issue 2.

Higashiyama et al., Novel functions and applications of trehalise, Pure Appl. Chem. 2002, pp. 1263-1269, vol. 74, No. 7.

Nakamoto et al., The small heat shock proteins and their clients, Cell. Mol. Life Sci, 2007, pp. 294-306, vol. 64.

Sampath, T.K., "Bovine Osteogenic Protein is Composed of Dimers of OP-1 and BMP-2A, Two Members of the Transforming Growth Factor-Beta Superfamily", J Biol Chem, 1990, pp. 13198-13205, vol. 265, Issue 22.

Triantfilou et al., A CD14-independent LPS receptor cluster, Nature Immunology, 2001, 338-345, vol. 2.

Wang et al., Instability, stabilization, and formulation of liquid protein pharmaceuticals, International Journal of Pharmaceutics, 1999, pp. 129-188, vol. 185.

Arakawa et al., Pharmaceutical Research "Protein-Solvent Interactions in Pharmaceutical Formulations", vol. 8, No. 3, 1991, pp. 285-291.

Brus, C. et. al., "Stabilization of Oligonucleotide-Polyethylenimine Complexes by Freeze-Drying: Physicochemical and Biological Characterization". Journal of Controlled Release, Feb. 20, 2004, vol. 95, Issue 1, pp. 119-131.

Cheng, Hongwei. "Osteogenic Activity of the Fourteen Types of Human Bone Morphogenic Proteins", Journal Bone Joint Surgery Am. 85A, 2003, pp. 1544-1552.

Costantino, Henry R. et. al., "Effect of Excipients on the Stability and Structure of Lyophilized Recombinant Human Growth Hormone", Journal of Pharmaceutical Sciences, 1998, vol. 87, Issue 11, pp. 1412-1420.

Crowe, J., "Stabilization of Dry Phospholipid Bilayers and Proteins by Sugars", Biochem. J., 1987, 242, pp. 1-10.

Gloger, O., "Lyoprotection of Aviscumine with Low Molecular Weight Dextrans", International Journal of Pharmaceutics, Jul. 9, 2003, vol. 260, Issue 1, pp. 59-68.

Goodnough, M C, et. al., "Stabilization of Botulinum Toxin Type A During Lyophilization", Applied Environmental Microbiology, 1992, vol. 58, Issue 10, pp. 3426-3428.
Honda et al. Jouranl of Bioscience and Bioengineering 89(6), 582-589 (2000).
Lories, Rik, J. U., "Bone Morphogenetic Protein Signaling in Joint Homeostasis and Disease", Cytokine Growth Factor Review, vol. 16, Issue 3, 2005, pp. 287-298.
Lyons, K et. al., "Vgr-1, a Mammalian Gene Related to Xenopus Vg-1, is a M Member of the Transforming Growth Factor Beta Gene Superfamily", Proceedings of the National Academy of Science, 1989, vol. 86, Issue 12, pp. 4554-4558.
Massague, et al. Annual Review of Cell Biology, 6:957 (1990).
Massague, J., "The Transforming Growth Factor-beta Family", Annual Review of Cell Biology, Nov. 1990, vol. 6, pp. 597-641.
Ozkaynak et. al., "OP-1 cDNA Encodes an Osteogenic Protein in the TGF-Beta Family". EMBO Journal, 1990, vol. 9, Issue 7, pp. 2085-2093.
Ramos et. al., "Stabilization of Enzymes Against Thermal Stress and Freeze-Drying by Mannosylglycerate", Appl. Envir. Microiol. 1997, vol. 63, Issue 10, pp. 4020-4025.
Ruppert, et al. Eur J Biochem 237, 295-302 (1996).
Wharton, KA et. al., "*Drosophila* 60A Gene, Another Transforming Growth Factor Beta Family Member, is Closely Related to Human Bone Morphogenetic Proteins", Proceedings of the National Academy of Science, 1991, vol. 88, Issue 20, pp. 9214-9218.
Yancey, Paul, "Organic Osmolytes as Compatible, Metabolic and Counteracting Cytoprotectants in High Osmolarity and Other Stresses" Journal of Experimental Biology, 2005, vol. 208, pp. 2819-2830.
Cryobiology and Cryotechnology, 2003, vol. 48, No. 2, pp. 139-143 (English equivalent WO02/066096).
Reito, 2004, vol. 79, No. 915, pp. 45-48 (English equivalent WO02/066096).
Pharmaceutical Research, 1991, vol. 8, No. 3, pp. 285-291.

* cited by examiner

Figure 1: DSC profile of rhGDF-5 /trehalose formulation, example 6
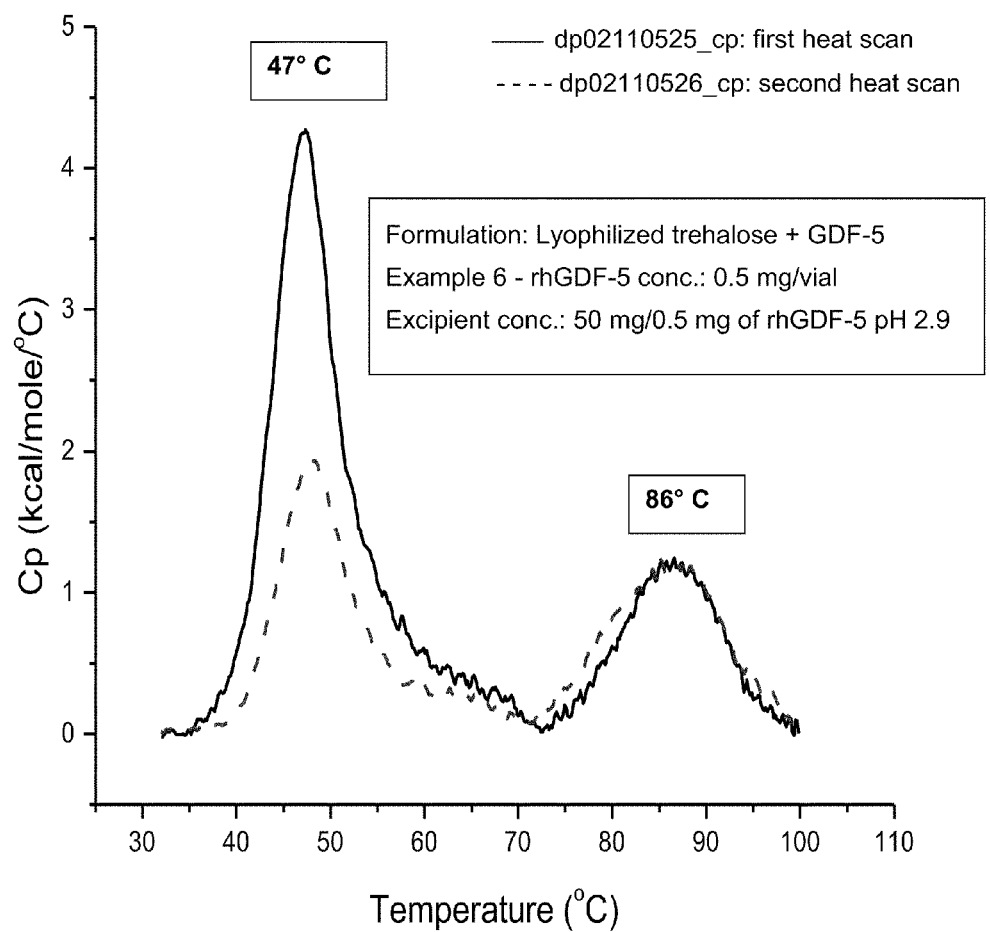
The lyophilized formulation was reconstituted with water. The final concentration was 0.33 mg/ml of protein + 3.3 % trehalose.

Figure 2: DSC profile of rhGDF-5 /mannitol formulation, example 7
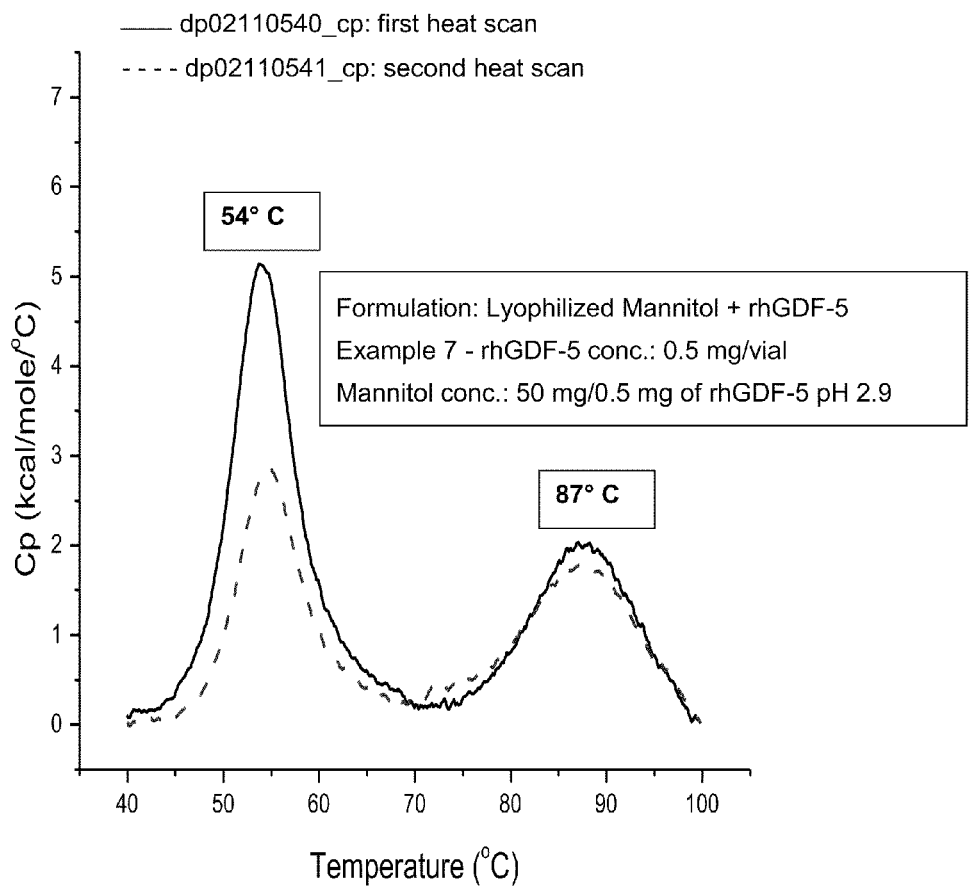
The lyophilized formulation was reconstituted with water. The final concentration was 0.33 mg/ml of protein + 3.3 % Mannitol.

Figure 3: DSC profile of rhGDF-5 native protein
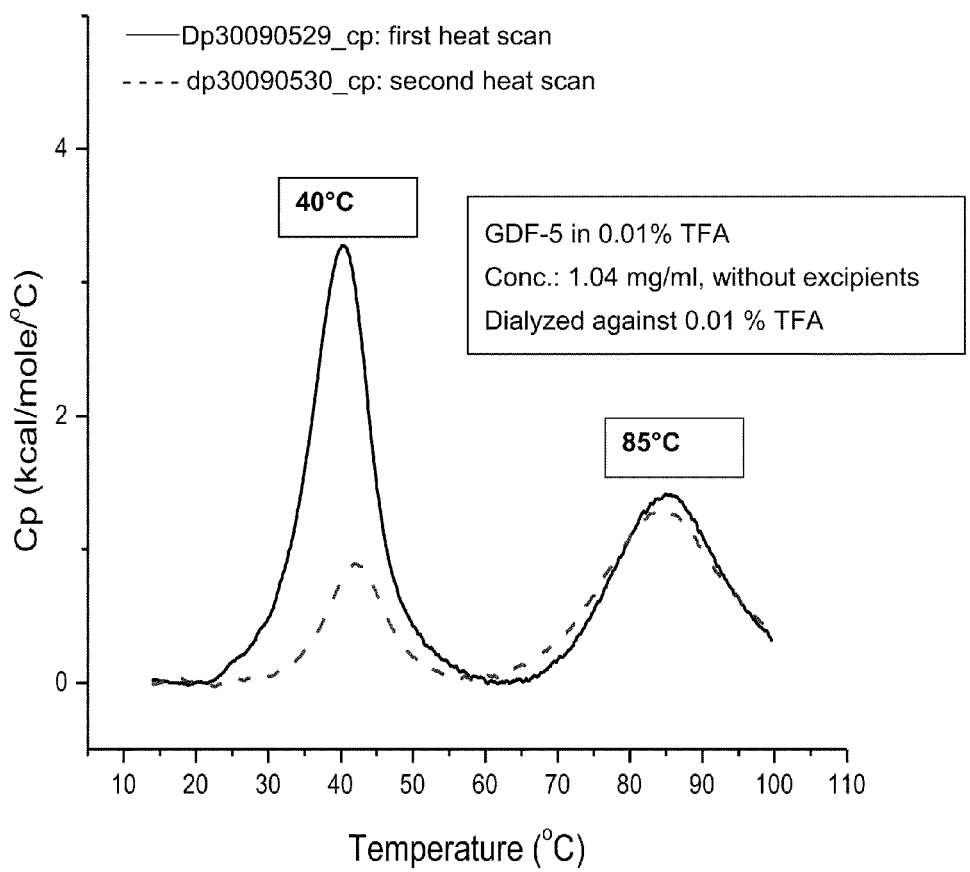
Bulk GDF-5, 3.8 mg/ml in 10 mM HCl was dialyzed against 0.01 % TFA. Final protein concentration was 1.04 mg/ml.

Figure 4: Polarized light Microscopy of the trehalose/GDF-5 formulation, example 6, showing the desirable amorphous state of the trehalose.
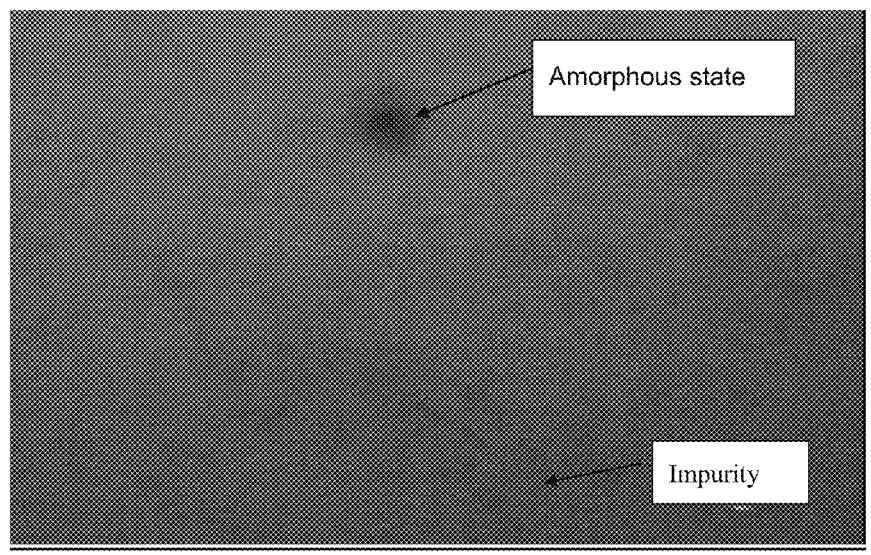
Lyophilized formulation: example 6, rhGDF-5 conc.: 0.5 mg/vial, trehalose 50 mg/ 0.5 mg of rhGDF-5, pH 2.9

Figure 5: Polarized light Microscopy of the Mannitol/GDF-5 formulation, example 7, showing the undesirable crystallized state of mannitol.
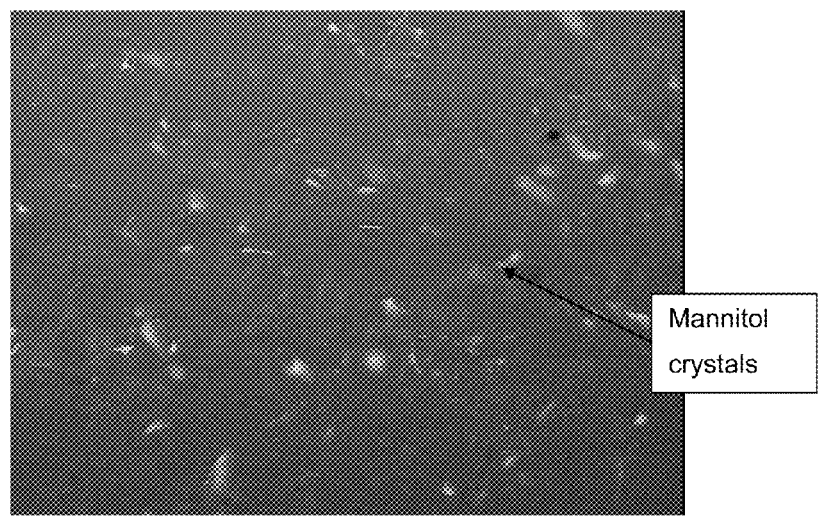
Lyophilized formulation: example 7, rhGDF-5 conc.: 0.5 mg/vial, Mannitol 50 mg/ 0.5 mg of rhGDF-5, pH 2.9

Figure 6: rpHPLC of the rhGDF-5/trehalose/Glycine formulation after 6 months at 40°C/75% RH.
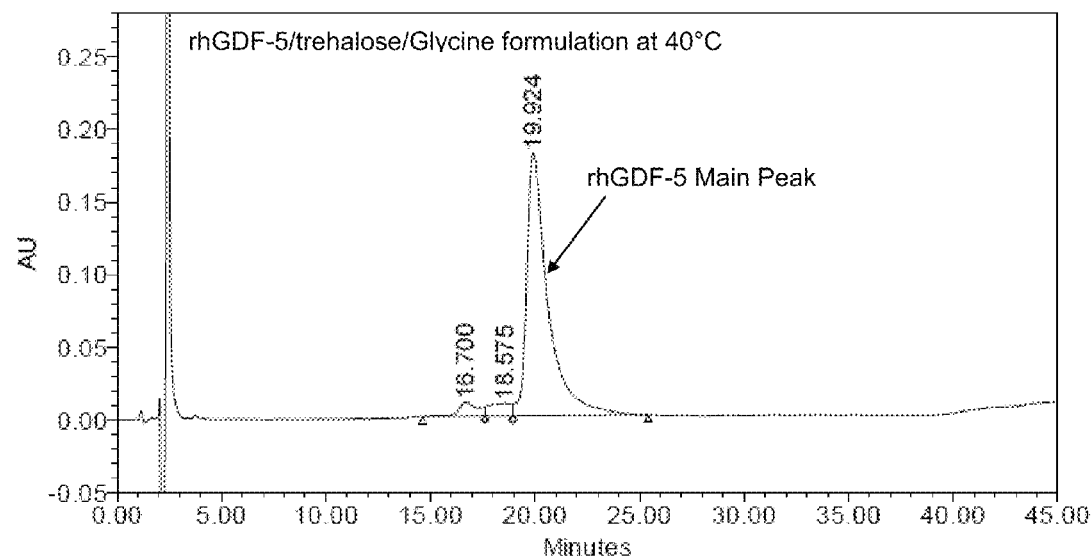
Figure 7: rpHPLC of the rhGDF-5/trehalose/HCl formulation after 6 months at 40°C/75% RH.
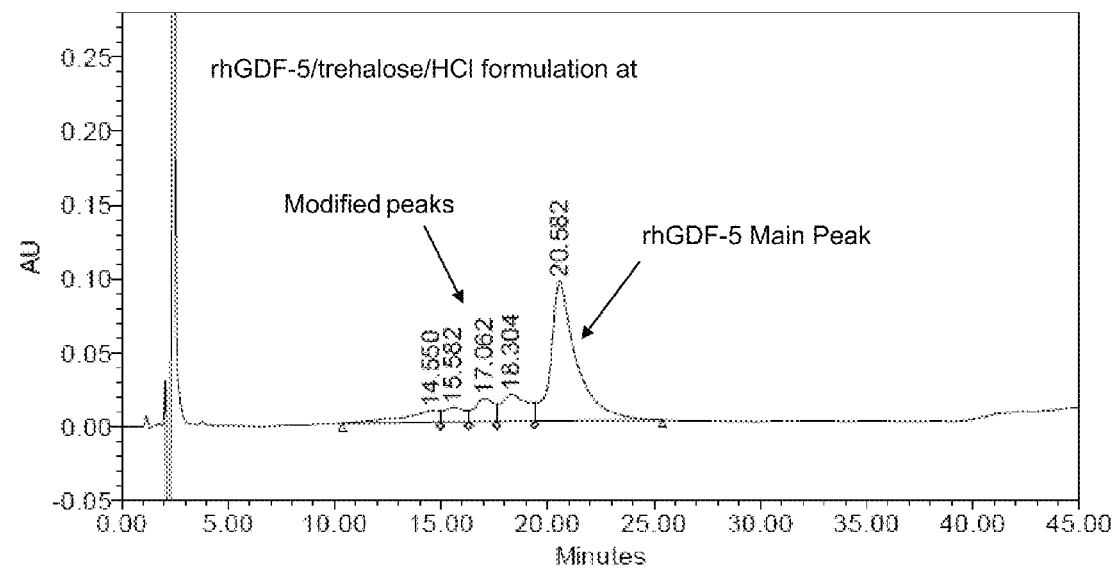

Figure 8: Stability of rhGDF-5 lyophilized with various buffer systems at pH3 after storage at 5°C.
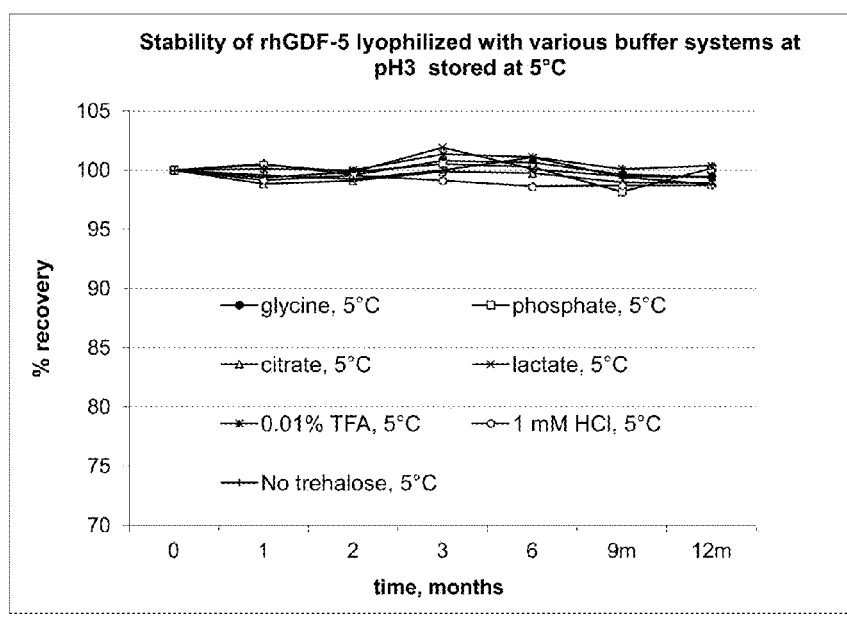

Figure 9. Stability of rhGDF-5 Lyophilized with various buffer systems at pH 3 after storage at 25°C.
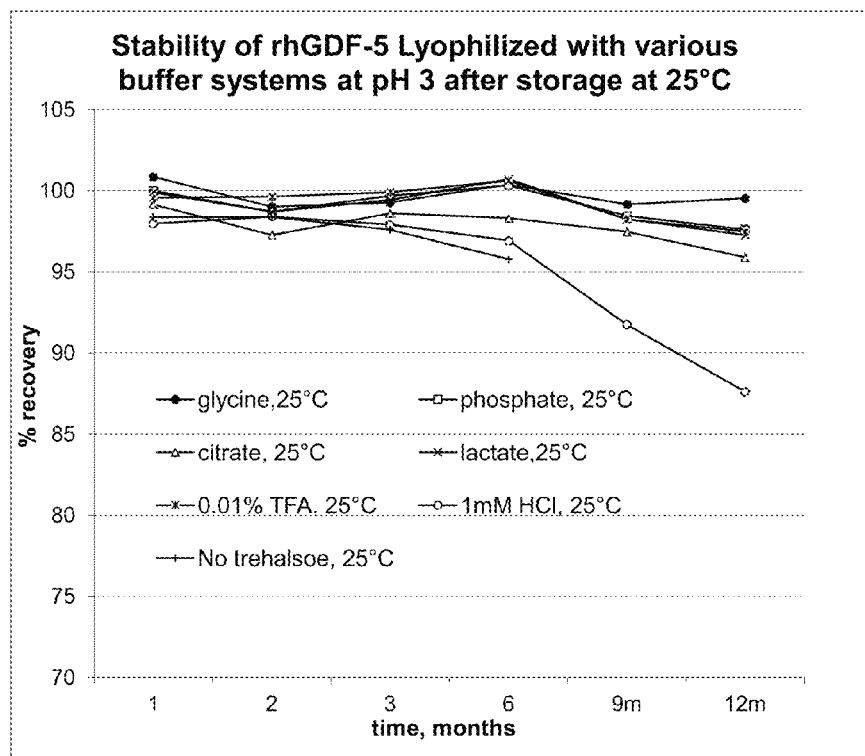

Figure 10. Stability of rhGDF-5 Lyophilized with various buffer systems at pH 3 after storage at 40°C.
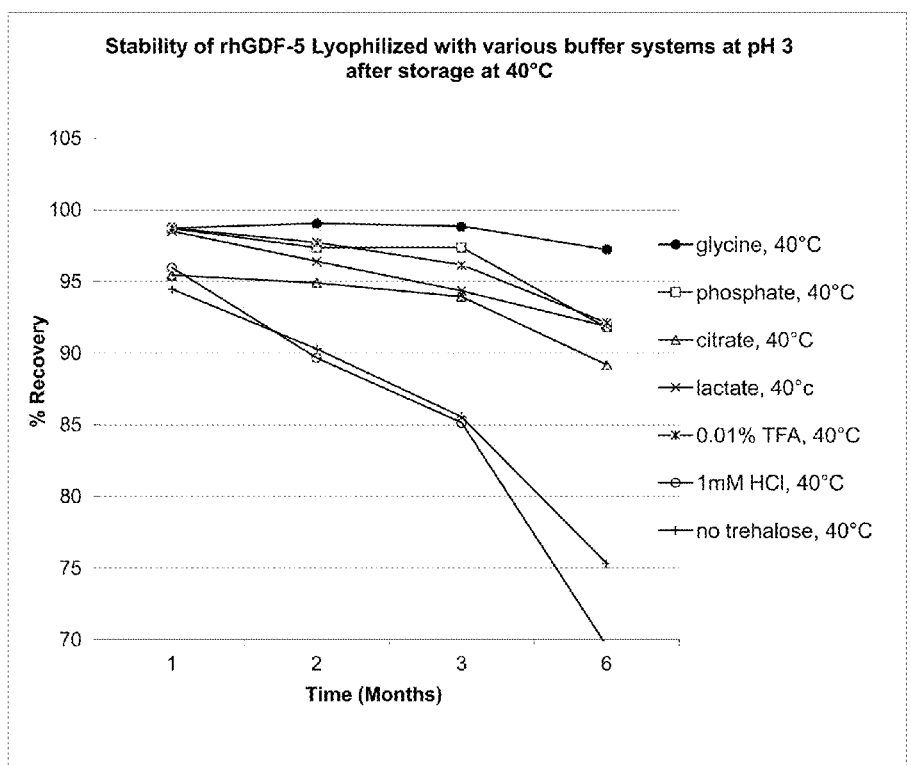

Figure 11. Stability of Various Concentrations of rhGDF-5 at Selected Temperatures Lyophilized With 5% or 10% Trehalose in pH3 Glycine Buffer.
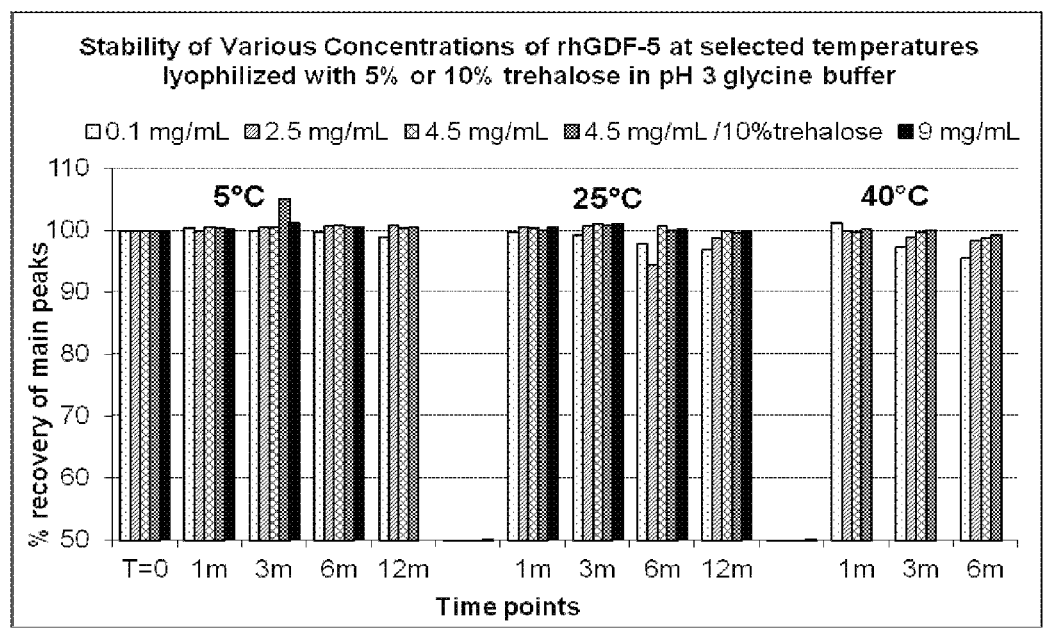

PROTEIN STABILIZATION FORMULATIONS

RELATED APPLICATION

This application is a divisional of U.S. application Ser. No. 11/950,127 entitled "PROTEIN STABILIZATION PORMULATIONS", filed on Dec. 4, 2007, now U.S. Pat. No. 7,956,028 which is a non provisional of provisional filing, U.S. App. Pat. No. U.S. App. Pat. No. 60/870,032 entitled "PROTEIN STABILIZATION FORMULATIONS," filed on Dec. 14, 2006.

FIELD OF THE INVENTION

The present invention is directed toward formulations and methods for stabilizing bone morphogenetic proteins (BMP's) and the closely related growth and differentiation factors (GDF's) during processing, storage, and reconstitution. More particularly, the present invention relates to formulations comprised of trehalose and other excipients to protect rhGDF-5 during lyophilization, storage, and reconstitution, including various substrates used as a vehicle to deliver rhGDF-5. Additionally, the present invention includes methods for preparing and using such formulations to treat various musculoskeletal defects and conditions.

BACKGROUND OF THE INVENTION

Biological molecules (biomolecules) have three-dimensional structure or conformation, and rely on this structure for their biological activity and properties. Examples of such biomolecules include deoxyribonucleic acid (DNA), ribonucleic acid (RNA), and proteins. These biomolecules are essential for life, and represent therapeutic agents and targets in treating various medical diseases and conditions. Proteins represent a broad class of biomolecules. Different classes of proteins such as enzymes, growth factors, receptors, antibodies, and signaling molecules depend on their conformational structure for their biological activity. Other classes of proteins are primarily structural, e.g. collagen and cartilage, and do not possess biological activity per se.

Exposing biomolecules to various environments such as variations in pH, temperature, solvents, osmolality, etc., can irreversibly change or denature the conformational state of the biomolecule, rendering it biologically inactive. Some of the mechanisms involved in the deactivation of these biomolecules include aggregation, oxidation, various types of bond cleavage including hydrolysis and deamidation, and various types of bond formation, including cross-linking and other covalent binding, for example the rearrangement of disulfide bonds.

Bone morphogenetic proteins and the closely related growth and differentiation factors (in both monomeric and dimeric forms) belong to the TGF-β superfamily of proteins. This class of proteins includes members of the family of bone morphogenetic proteins that were initially identified by their ability to induce ectopic endochondral bone formation (see Cheng et al. "Osteogenic activity of the fourteen types of human bone morphogenic proteins" *J. Bone Joint Surg. Am.* 85A: 1544-52 (2003)). There are alternate names for several of these proteins, (see Lories et al., *Cytokine Growth Factor Rev* 16:287-98 (2005)). All members of this family share common structural features, including a carboxy terminal active domain, and are approximately 97-106 amino acids in mature length. All members share a highly conserved pattern of cysteine residues that create 3 intramolecular disulfide bonds and one intermolecular disulfide bond. The active form can be either a disulfide-bonded homodimer of a single family member or a heterodimer of two different members. (see Massague *Annu. Rev. Cell Biol.* 6:957 (1990); Sampath, et al. *J. Biol. Chem.* 265:13198 (1990); Ozkaynak et al. *EMBO J.* 9:2085-93 (1990); Wharton, et al. *PNAS* 88:9214-18 (1991); Celeste et al. *PNAS* 87:9843-47 (1990); Lyons et al. *PNAS* 86:4554-58 (1989), U.S. Pat. No. 5,011,691, and U.S. Pat. No. 5,266,683).

It is well established that many sugars stabilize biomolecules in solution and afford protection to isolated cells and biomolecules. These compounds are well established as cryoprotectants and osmoregulators in various species (see Yancey *J. Exper. Biol.* 208: 2819-30 (2005)). In the development of lyophilized pharmaceutical proteins, sugars (saccharides and polyols) are often added to the formulation in order to improve the stability of the protein and prolong the shelf life. There are two main theories on the mechanism of the stabilizing action of sugars: 1) the sugar excipients serve to dilute the proteins in the solid state, thereby decreasing protein-protein interactions and preventing molecular degradation, such as aggregation, and 2) the sugar excipients provide a glassy matrix wherein protein mobility and hence reactivity are minimized. In both of these mechanisms, it is critical that the sugar remains in the amorphous, protein-contacting phase. Various environmental factors, such as increased temperature and moisture, can induce sugar crystallization. Thus, it is important to optimize the conditions and materials used to suit the particular biomolecule and system under consideration.

Lyophilization (freeze-drying) is a method commonly used to preserve biomolecules. Freeze-drying is generally thought to be more disruptive to the biological activity of biomolecules than freeze-thawing or temperature-induced denaturation. The magnitude of damage varies considerably with different biomolecules and different conditions, and various investigators have studied different systems. The freezing of aqueous solutions creates an initial increase in solute concentrations that can be more damaging to labile compounds than the freezing itself. Excipients such as sugars, proteins, polymers, buffers, and surfactants can be added to stabilize the activity of the biomolecule, but have limited and varying degrees of success, depending on the system. Crowe, et al. describes the stabilization of dry phospholipid bilayers and proteins by sugars (*Biochem. J.* 242: 1-10 (1987)), and also reviews the recent understanding of the mechanisms of trehalose stabilization of cells in "The trehalose myth revisited: Introduction to a symposium on stabilization of cells in the dry state" *Cryobiology* 43, 89-105 (2001). The current thinking is that there are two separate and different requirements for maintaining a viable and useful lyophilized protein: 1) the protein must be protected during the freezing process, and 2) the protein must be protected during the subsequent drying and reconstitution. These are different requirements that are not necessarily met by any one excipient or set of conditions.

Various researchers have reported on using various excipients to protect various biomolecules, for example Gloger, et al. (*Intl. J. Pharm.* 260: 59-68 (2003)) described the lyoprotection of aviscumine using low molecular weight dextrans to stabilize the protein, and showed that the buffer system and polysorbate 80 alone are suitable to protect the protein during freezing, but dextran is needed to protect the protein during drying; Goodnough, et al. (*Appl. Env. Biol.* 58(10: 3426-28 (1992)) investigated the stabilization of Botulinum toxin type A during lyophilization using serum albumin as stabilizer and various other excipients, and reported that none of the excipients had any beneficial effect, but by eliminating NaCl from the lyophilization mixture and by controlling the pH, the recovery of active toxin was dramatically improved; Costantino, et al. (*J. Pharm. Sci.* 87(11): 1412-20 (1998)) described the effects of various saccharides on the stability and structure of lyophilized recombinant human growth hormone, and showed that all of the excipients tested significantly improved the stability of the protein; Ramos et al. (*Appl. Envir. Microbiol.* 63(10): 4020-25 (1997)) showed that 2-O-β-mannosylglycerate is effective in protecting several dehydrogenase enzymes isolated from various sources from thermal stress, and that the protection afforded by 2-O-β-mannosylglycerate was similar to or superior to trehalose for all of the enzymes studied, but was not effective in protecting glutamate dehydrogenase isolated from *P. furiosis*; Brus, et al. (*J. Control. Rel.* 95:119-31 (2004)) investigated the stabilization of oligonucleotide-polyethylenimine (PEI) complexes by freeze-drying, and reported that these complexes did not benefit from the addition of sugars such as sucrose or trehalose, but that plasmid-PEI complexes did benefit from the addition of such sugars. These investigators report varying degrees of success, as measured by various methods on various biomolecules. None of these investigators have reported on the protection of BMP's.

Thus, there is conflicting evidence on what is an optimal combination of excipients to afford lyoprotection of biomolecules. There is not any one combination of excipients that is optimal for all biomolecules, but rather a significant degree of experimentation is required to obtain the desired results for the biomolecule under investigation. There remains a need for a pharmaceutically acceptable combination of excipients to protect BMP's during lyophilization, storage, and use.

BRIEF DESCRIPTION OF THE DRAWINGS

FIG. 1 shows the DSC profile of the trehalose formulation of rhGDF-5 as described in example 6.

FIG. 2 shows the DSC profile of the mannitol formulation of rhGDF-5 as described in example 7.

FIG. 3 shows the DSC profile of rhGDF-5 native protein.

FIG. 4 shows the polarized light microscopy of the trehalose formulation of rhGDF-5 as described in example 6.

FIG. 5 shows the polarized light microscopy of the mannitol formulation of rhGDF-5 as described in example 7.

FIG. 6 shows the rpHPLC profile of the rhGDF-5/trehalose/Glycine formulation after 6 months at 40° C./75% RH as described in example 12.

FIG. 7 shows the profile of the rpHPLC of the rhGDF-5/trehalose/HCl formulation after 6 months at 40° C./75% RH as described in example 12.

FIGS. 8, 9, and 10 show the % protein recovery of the various buffers tested at storage at 5°, 25°, and 40° C. at various time points, as described in example 12.

FIG. 11 shows the stability of Various Concentrations of rhGDF-5 at Selected Temperatures Lyophilized With 5% or 10% Trehalose in pH3 Glycine Buffer, as described in example 14.

SUMMARY OF THE INVENTION

The present invention is generally directed to stabilizing BMP's in various formulations and compositions, thereby preserving at least 60% of the biological activity and improving the storage condition requirements, for example temperature and humidity. The present invention comprises formulations primarily including trehalose as an excipient for lyophilized compositions containing BMP and their subsequent storage and reconstitution, and further comprising other excipients including buffers and surfactants.

The present inventors have surprisingly discovered that trehalose is sufficient and superior to other excipients to preserve the biological activity of BMP's during and after lyophilization. In the stabilization of many other biomolecules there is little difference among sugars as to the amount of protection afforded, but for BMP's there is a great difference. This discovery provides for compositions to treat various musculoskeletal defects in a patient without the potential for adverse reactions to additional excipients. The present inventors have also surprisingly discovered that the addition of antioxidants such as ascorbic acid and glutathione do not increase the stability of the BMP lyophilized with trehalose, but rather detracts from the stability afforded by trehalose.

It is an object of the invention to utilize trehalose in an amount that is sufficient to stabilize a lyophilized BMP, such that the BMP retains at least 60% of the biological activity upon rehydration, with said rehydrated liquid product being easily handled by the surgeon.

It is another object of the invention to utilize trehalose in an amount that is sufficient to stabilize a lyophilized BMP, at least one BMP, and additional excipients, said additional excipients selected from the group consisting of a buffer, a surfactant and mixtures thereof, such that the BMP retains at least 60% of the biological activity upon rehydration, with said rehydrated liquid product being easily handled by the surgeon.

It is another object of the invention to utilize trehalose in an amount that is sufficient to stabilize a lyophilized BMP, at least one BMP, and morselized collagen fibers to provide compositions and methods of preparing a lyophilized biocompatible flowable material containing BMP that is stable and retains at least 60% of the biological activity upon rehydration, such that the rehydrated product can be easily handled by the surgeon.

It is another object of the invention to utilize trehalose in an amount that is sufficient to stabilize a lyophilized BMP, at least one BMP, and a biocompatible matrix to provide compositions and methods of preparing a lyophilized biocompatible matrix containing BMP that is stable and retains at least 60% of the biological activity upon rehydration, such that the rehydrated product can be easily handled by the surgeon. Exemplary biocompatible matrices include collagen, mineralized collagen, salts of calcium phosphate, ceramics containing calcium, bone from various sources including autogenic, allogenic, and xenogenic, and polymers, including polylactide (PLA), polyglycolide (PGA), PLA-PGA co-polymers, polycarbonate, polycaprolactone and mixtures thereof.

It is another object of the invention to utilize trehalose in an amount that is sufficient to stabilize a lyophilized BMP, at least one BMP, a biocompatible matrix, and additional excipients, said additional excipients selected from the group consisting of a buffer, a surfactant and mixtures thereof, to provide compositions and methods of preparing a lyophilized biocompatible matrix containing BMP that is stable and retains at least 60% of the biological activity upon rehydration, such that the rehydrated malleable product can be easily handled by the surgeon.

It is another object of the invention to utilize one or more lyoprotectants selected from the group consisting of trehalose, low molecular weight dextran, cyclodextrin, polyethylene glycol, polyethylene glycol ester and mixtures thereof, in an amount that is sufficient to stabilize a lyophilized BMP, and at least one BMP to provide compositions and methods of preparing a lyophilized BMP, such that the BMP retains at least 60% of the biological activity upon rehydration, with said rehydrated product being easily handled by the surgeon.

It is another object of the invention to utilize one or more lyoprotectants selected from the group consisting of trehalose, low molecular weight dextran, cyclodextrin, polyethylene glycol, polyethylene glycol ester and mixtures thereof, at least one BMP, and collagen to provide compositions and methods of preparing a lyophilized biocompatible collagen matrix containing BMP that is stable and retains at least 60% of the biological activity upon rehydration, such that the rehydrated malleable product can be easily handled by the surgeon.

It is another object of the invention to utilize one or more lyoprotectants selected from the group consisting of trehalose, low molecular weight dextran, cyclodextrin, polyethylene glycol, polyethylene glycol ester and mixtures thereof, at least one BMP, and morselized collagen fibers to provide compositions and methods of preparing a lyophilized biocompatible flowable material containing BMP that is stable and retains at least 60% of the biological activity upon rehydration, such that the rehydrated product can be easily handled by the surgeon.

It is still another object of the invention to treat a patient utilizing a composition comprised of a lyophilized mixture of at least one lyoprotectant and at least one BMP. Such compositions are useful in treating a variety of musculoskeletal defects in order to enhance the healing process, either by directly applying the reconstituted BMP solution to a region of the anatomy of a patient, such as for example to a bone fracture, a bone gap, a bone void, an intervertebral disc, a chondral defect, a tendon, a ligament, and the like, or applying the reconstituted BMP solution to a device to be implanted into the patient, for example a bone-contacting artificial implant such as an artificial hip, knee, shoulder, intervertebral disc, and the like, a tendon anchor, ligament anchor, suture, staple, and the like, a bone replacement cage, autologous bone chips, allogenic bone chips, xenogenic bone chips, demineralized bone chips, and the like.

Bulk forms of BMP in either aqueous solution or as a dry solid are not stable, and require cold storage below $-20°$ C. to preserve the biological activity of the protein. Since BMP is susceptible to aggregation, rearrangement of disulfide bonds, deamidation, and oxidation, a need is present for a formulation to preserve and protect the biological activity of lyophilized BMP.

There is a need for a lyophilized BMP product with improved stability and storage.

There is a need for a lyophilized BMP product for reconstitution with aqueous solutions to be used for injection into soft tissue such as the intervertebral disc, non-articular and articular cartilage to promote regeneration of such tissues.

There is a need for a lyophilized BMP product that is provided on an implantable biocompatible scaffold with the proper concentration of BMP for the physician to use, thereby minimizing or eliminating many of the risks associated with handling, including contamination, improper dosage, and spillage, including waste and introduction to an undesired surgical site.

There is a need for a lyophilized BMP product that can be reconstituted in a biocompatible flowable material that can be easily applied to a surgical site.

DETAILED DESCRIPTION OF THE INVENTION

Since the discovery of BMP, there has been considerable research activity to find a suitable composition for their therapeutic use in treating a variety of musculoskeletal defects and conditions. Currently there are products containing BMP that are sold as a lyophilized solid, which must be reconstituted to a liquid form and applied by the physician to the scaffold to be implanted or to the surgical treatment site at the time of use. The current formulation of rhBMP-2 uses sucrose NF, glycine USP, L-glutamic acid FCC, sodium chloride USP, and polysorbate 80 NF as excipients, and may be stored at room temperature (15-25° C.). The current formulation of OP-1 uses bovine collagen alone, and must be stored at 2-8° C. There are no published reports that describe the efficacy of excipients on the stability of the reconstituted BMP.

Others have attempted to enhance the stability of BMP during lyophilization by using mannitol, sucrose, and mixtures thereof, by embedding the BMP in polymer matrices such as PLGA, by adding anti-oxidants such as methionine, by adding other excipients such as histidine, arginine, cyclodextrin, and bovine serum albumin, and by adding surfactants such as TWEEN 80, or combinations thereof. These attempts have met with varied degrees of limited success.

U.S. Pat. Nos. 5,318,898 and 5,516,654 disclose improved processes of producing BMP by using dextran sulfate in the culture medium, but do not discuss the mechanism of how the benefit is achieved or disclose any other useful excipients to stabilize the proteins. In U.S. Pat. No. 5,385,887 Yim et al. disclose lyophilized compositions and formulations for the delivery of BMP, with said compositions comprised of a BMP, a sugar, glycine, and glutamic acid. Although Yim et al. disclose that the lyophilized formulations retain biological activity as evidenced by the W-20 Alkaline Phosphatase Assay, they do not disclose comparative data on the formulations to show any quantitative benefits of any one formulation over another. These inventors do not discuss or recognize the superiority of trehalose over sucrose for lyoprotection of the BMP.

The present invention provides for compositions and methods of preparing and using stable formulations of BMP, useful for lyophilization, storage, and reconstitution with an aqueous solution to treat a patient therewith. The present invention is described below relative to illustrative embodiments, and utilizes rhGDF-5 as the exemplary BMP. Those skilled in the art will appreciate that the present invention may be implemented in a number of different applications and embodiments and is not specifically limited in its application to the particular embodiments depicted herein. The following examples illustrate some of the various embodiments and benefits of the present invention, however one skilled in the art will appreciate that other similar embodiments can be made without deviating from the scope and intent of the present invention.

The present invention provides, in one aspect, a composition and method for preparing a stable lyophilized BMP for subsequent use in the surgical treatment of bone and cartilage defects. As contemplated herein, such a composition comprises at least one BMP and trehalose in an amount sufficient to stabilize the BMP. Such compositions are useful in treating a variety of musculoskeletal defects by directly applying the reconstituted protein solution either directly to a region of the anatomy of a patient, such as for example to a bone fracture, a bone gap, a bone void, an intervertebral disc, an intervertebral disc space as surgically prepared for fusion, a chondral defect, a tendon, a ligament, and the like, or to a material to be implanted into the patient in contact with bone or cartilage, such as an artificial hip, an artificial knee, an artificial shoulder, an artificial intervertebral disc, a tendon anchor, a ligament anchor, a suture, a staple, a bone cage, autologous bone chips, allogenic bone chips, xenogenic bone chips, demineralized bone chips, and the like.

As used herein, the terms "morphogen", "bone morphogen", "bone morphogenic protein", "bone morphogenetic protein", "BMP", "osteogenic protein", "osteogenic factor", "Growth & Differentiation Factor", and "GDF" embrace the class of proteins typified by rhGDF-5. It will be appreciated by one having ordinary skill in the art, however, that rhGDF-5 is merely representative of the TGF-β family subclass of true tissue morphogens capable of acting as BMP, and is not intended to limit the description. The term "cryoprotectant" is used to refer to a molecule capable of stabilizing a biomolecule during freezing, and is equivalent in the current context with the term "lyoprotectant", which refers to a molecule capable of stabilizing a biomolecule during freeze-drying (lyophilization). As used herein, the term "morselized" refers to the product obtained by, and "morselization" to the process of cutting, chopping, severing, grinding, pulverizing, or otherwise reducing the size of an amount of a biocompatible matrix, for example collagen, such that the overall size of the individual particles or fibers are reduced. As used herein, the term "excipient" refers to at least one additional compound added to at least one BMP, with said additional compound selected from the group consisting of amino acids, proteins, buffers, surfactants and mixtures thereof. The terms "ceramic" and "ceramics containing calcium" are understood to mean synthetic bone substitute materials known in the art, and include for example Bioglass™ and various compositions containing primarily silica, alumina, and mixtures thereof, with smaller amounts of calcium, barium, strontium, magnesium, carbonate, sodium, potassium, fluoride, and other ions used to modify the properties of the synthetic bone material. The term "salts of calcium phosphate" is understood to mean various compositions of calcium phosphate useful for bone substitute materials, including, but not limited to hydroxyapatite, tricalcium phosphate, brushite, monetite, and various other stoichiometric ratios of calcium and phosphate useful for bone substitute materials, including calcium phosphate compositions with the addition of smaller amounts of other ions, such as magnesium, barium, strontium, carbonate, sodium, potassium, fluoride, etc. to modify the properties, as is commonly known in the art.

It has been known that rhGDF-5 has poor solubility at neutral pH in the range of pH 4.5 to pH 10.5. It would be difficult to formulate and manufacture rhGDF-5 products in this pH range. Therefore the inventors designed a study to evaluate the solubility of rhGDF-5 in pH 3 and pH 4 buffers, which is critical to select a suitable pH range for the development of protein formulations. The study results are described in example 11. The solubility of rhGDF-5 depends not only on the pH of the buffer, but also depends on the ionic strength of the buffer solution. At pH 4, the rhGDF-5 solutions at approximately 10 mg/mL were hazy in 5 and 10 mM sodium phosphate buffers, while in 50 and 100 mM sodium phosphate buffers the rhGDF-5 formed large particles and finally precipitated out. In another study (data not shown) when rhGDF-5 was formulated at 3.5 mg/mL at pH 3.5 and pH 4 of 5 mM phosphate buffer, the solutions were also hazy.

The solubility of a protein substance is usually determined by measuring the protein concentration after centrifugation or filtration of an over saturated/precipitated solution. However, some hazy protein solutions are difficult to centrifuge or filter. Even after a hazy solution is subjected to centrifugation or filtration (0.22 μm) to remove the insoluble particles, quite often it is unsuccessful as the filtrate still looks hazy because the particles are so fine and some times the protein sticks to filter surface, thus the filtrate loses most of the protein. Therefore, it would be difficult to get a clear solution when rhGDF-5 is formulated at 3.5 mg/mL or 10 mg/mL in pH 3.5 or pH 4 buffers.

When rhGDF-5 was formulated at 10 mg/ml in 5 mM, 10 mM and 25 mM sodium phosphate solutions at pH 3.0, the protein solution was clear; but rhGDF-5 at 10 mg/ml in higher ionic strength solutions such as 50 mM and 100 mM sodium phosphate, the rhGDF-5 solutions were hazy. Thus, in a preferred embodiment the rhGDF-5 should be formulated in a low ionic strength buffer at approximately pH 3.0.

In one embodiment according to the present invention the composition can be prepared by lyophilizing an aqueous mixture of at least one BMP together with an amount of trehalose sufficient to stabilize the BMP, with the dry weight ratio of trehalose to BMP being in the range of about 1 mg to about 500 mg trehalose per 1 mg BMP, and more preferably in the range of about 5 mg to about 200 mg trehalose per 1 mg BMP for biocompatible matrix containing products. The addition of trehalose provides for improved solubility and stability of the protein in lyophilized formulations. Lyophilization is performed according to the practice as generally known in the art.

In another embodiment the composition according to the present invention can be prepared by lyophilizing an aqueous mixture of at least one BMP, an amount of trehalose sufficient to stabilize the BMP, and a buffering agent. The addition of a buffering agent provides for improved solubility and stability of the protein in lyophilized formulations. Biocompatible buffering agents known in the art include glycine; sodium, potassium, or calcium salts of acetate; sodium, potassium, or calcium salts of citrate; sodium, potassium, or calcium salts of lactate; sodium or potassium salts of phosphate, including mono-basic phosphate, di-basic phosphate, tri-basic phosphate and mixtures thereof. The buffering agents could additionally have glycine added to the composition to function as a bulking agent. The glycine would be added in a ratio of about 0.04 mg to about 200 mg glycine per 1 mg BMP, and more preferably from about 1 mg to about 80 mg glycine per 1 mg BMP. The addition of buffering and bulking agents provides for slightly superior stability of the protein over compositions having trehalose alone, with the pH being controlled within about 2.0 to about 5.0 pH units, and more preferably within about 2.5 to about 3.5 pH units.

In an alternate embodiment the composition and method according to the present invention can be prepared by lyophilizing an aqueous mixture of at least one BMP, an amount of trehalose sufficient to stabilize the BMP, a buffering agent, and a surfactant selected from the group consisting of polysorbate 80, polysorbate 20 and mixtures thereof. The surfactant would be added in a concentration of from about 0.001 mg to about 0.2 mg per 1 mg of BMP. The addition of surfactant provides additional stabilization to the protein by altering the solubility and lyophilization characteristics. Lyophilization would be performed according to the practice as generally known in the art.

In another embodiment of the present invention, a composition and method for preparing a stable lyophilized BMP is comprised of at least one BMP, the lyoprotectant trehalose in an amount sufficient to stabilize the at least one BMP, and at least one additional excipient, said additional excipient selected from the group consisting of buffers and surfactants. The addition of such buffers and surfactants provides for an incremental improvement in the stability of the lyophilized BMP over compositions having trehalose as the sole excipient.

In an alternate embodiment, the composition and method according to the present invention can be prepared by depositing a solution of at least one BMP and at least one excipient onto lyophilized collagen prior to lyophilization of the BMP/collagen mixture. The collagen can optionally be either cross-linked or mineralized, or both cross-linked and mineralized, such as is provided by the material known as Healos® and described in U.S. Pat. Nos. 5,972,385; 5,866,165; 5,776,193; 5,455,231; and 5,231,169. The compositions provided in this embodiment are particularly useful in treating medical conditions in the field of orthopedics and provide a pliable, malleable material that the physician can easily place into a surgical site to generate bone, cartilage, or tendon. The BMP/collagen mixture can be reconstituted with aqueous solutions, including sterile water, saline solution, and bone marrow aspirate, and directly applied to defect sites in a patient, such as bone fractures, bone gaps, bone voids, the intervertebral disc space surgically prepared for spinal fusion. Additionally, the BMP/collagen mixture can be used for filling the space in between bone chips and implants placed into the intervertebral disc space during spinal fusion surgery, areas with damaged or missing cartilage, such as torn or damaged tendons, torn or damaged ligaments, chondral defects in articulating cartilage, and sub-chondral defects in articulating cartilage.

In an alternate embodiment, the composition and method according to the present invention can be utilized by preparing a lyophilized mixture of at least one BMP and at least one excipient, reconstituting the lyophilized BMP mixture with water, saline solution, or bone marrow aspirate, and placing the reconstituted BMP solution onto lyophilized collagen prior to surgical implantation of the BMP/collagen mixture. The collagen can optionally be either cross-linked or mineralized, or both cross-linked and mineralized, such as is provided by the material known as Healos®. The compositions and methods provided in this embodiment are particularly useful in treating medical conditions in the field of orthopedics and provide a pliable, malleable material that the physician can easily place into a surgical site to generate bone, cartilage, or tendon. The BMP/collagen mixture can be directly applied to defect sites in a patient, such as bone fractures, bone gaps, bone voids, the intervertebral disc space surgically prepared for spinal fusion, filling the space in between bone chips and implants placed into the intervertebral disc space during spinal fusion surgery, areas with damaged or missing cartilage, such as torn or damaged tendons, torn or damaged ligaments, chondral defects in articulating cartilage, and sub-chondral defects in articulating cartilage. The compositions and methods provided in this embodiment are also particularly useful for ease of storage and preparation by virtue of having the BMP as a separate component and container from the collagen material.

In an alternate embodiment the composition and method according to the present invention can be prepared by depositing a solution of at least one BMP and at least one excipient onto lyophilized morselized collagen prior to lyophilization of the BMP/morselized collagen mixture. The morselized collagen could optionally be either cross-linked or mineralized, or both cross-linked and mineralized. Such morselization provides for small collagen fibers of about 25 microns in diameter by about 110 microns length, which yields a flowable composition suitable for injection into a surgical site. Reconstitution of such a composition can be performed using a mixture of an aqueous solution such as sterile water, saline, or bone marrow aspirate, and collagen gel, with the collagen gel providing control of the viscosity of the reconstituted product. The collagen gel contains from about 0.1% to about 30% w/w collagen, and more preferably from about 0.3% to about 3.0% w/w collagen, with the viscosity of the collagen gel preferably from about 10 cP to about 400 cP, and more preferably from about 70 cP to about 100 cP. The pH of the collagen gel is preferably from about 4.0 pH units to about 8.0 pH units. Such a composition is useful for treating a variety of musculoskeletal conditions, including but not limited to bone fractures, bone gaps, bone voids, the intervertebral disc space surgically prepared for spinal fusion, filling the space in between bone chips and implants placed into the intervertebral disc space during spinal fusion surgery, areas with damaged or missing cartilage, such as torn or damaged tendons, torn or damaged ligaments, chondral defects in articulating cartilage, and sub-chondral defects in articulating cartilage.

In an alternate embodiment the composition and method according to the present invention can be utilized by preparing a lyophilized mixture of at least one BMP and at least one excipient, reconstituting the lyophilized BMP mixture with water or saline solution, and injecting the reconstituted BMP solution into the intervertebral disc. The compositions and methods provided in this embodiment are particularly useful in treating the intervertebral disc.

EXAMPLES OF THE INVENTION

In the following examples, the experimental methods used were as follows:

For RP-HPLC purity studies, reconstituted rhGDF-5 test samples were diluted to a concentration of 0.1 mg/ml with 10 mM HCl and subjected to reversed phase-HPLC on a Vydac 218TP52 column at 50° C. and a flow rate of 0.3 ml/min. rhGDF-5 is eluted using a gradient of acetonitrile in 0.15% trifluoroacetic acid using UV detection at 214 nm.

For Circular dichroism (CD) studies, Circular Dichroism was performed on an AVIV Model 60DS Circular Dichroism Spectropolarimeter. Baseline placebo runs with corresponding excipient scans were subtracted from the sample scans. The scans were normalized using Mean Residue Weight (value of 115) and inserting it into the equation:

$$[\Theta] = [0.1 \times M_{residue}]/[conc.(mg/ml) \times light\ path]$$

The value of $[\Theta]$ was calculated at each wavelength to give mean residue ellipticities. Finally, an estimate of secondary structure was determined using the program PROSEC v.2.1 (copyrighted in 1987 by AVIV Associates).

Differential scanning calorimetry (DSC) was performed on a MicroCal VP-DSC instrument. The scan rate was 60° C./h. The temperature range was 5-100° C. Instrument baseline scan (placebo data) was subtracted from test sample heat scan. The protein concentration was 0.33 mg/ml.

Polarized Light Microscopy (PLM) was used for Crystallinity Assessment. A trace amount of the solid sample was taken out of the vial in a dry air bag with a relative humidity of 1%. The solid sample was spread on a glass slide and one drop of silica oil was dropped onto the solid sample. Then the slide was investigated with a Zeiss Optical Microscope equipped with a Sony CCD-IRIS/RGB Color Video Camera and polarized light accessory. Flash Bus FBG software was used to capture images.

Bulk rhGDF-5 was received from Biopharm in a frozen format at −80° C. at a concentration of 3.8 mg/ml in 10 mM HCl. The frozen bulk protein was thawed over night at 2-8° C. before using in formulations.

Example 1

Healos® strips (non-sterile) with rhGDF-5 (0.5 mg/ml, 5 ml/strip) and trehalose 50 mg/ml. Each strip had 2.5 mg of rhGDF-5 and 250 mg of trehalose.

Preparation of Trehalose Solution:

25.48 g of trehalose dihydrate was carefully weighed and transferred into a sterile polypropylene bottle, to which 350 ml of purified water was added at room temperature and stirred slowly until a clear solution was obtained. To the clear solution, 0.1 N HCl was added drop by drop to adjust the pH to 3.9, then the volume was adjusted with purified water to obtain 400 ml final volume. The pH was measured and found to be 4.2. The solution was filtered through a 0.22-micron filter and was used directly to dilute the protein solution.

Dilution of rhGDF-5 Solution with Trehalose Solution:

22.39 ml of rhGDF-5 solution was carefully transferred to a polypropylene flask, to which trehalose solution was added carefully to adjust the volume to 150 ml; the pH was measured and found to be 2.5. The solution was stirred for 15 minutes at room temperature. The UV extinction coefficient was obtained to accurately calculate the protein concentration. Based on the UV reading, more trehalose solution was added to obtain the desired concentration of 0.5 mg/ml in 170 ml solution; the pH was measured and found to be 2.7; the UV reading indicated 0.499 mg/ml protein content.

The rhGDF-5/trehalose solution was filtered through a 0.22-micron filter and was used directly to dispense onto Healos® strips. Using sterile pipettes, 2.5 ml of rhGDF-5/trehalose solution was dispensed onto strips equally at 2 spots for a total of 5 ml of rhGDF-5/trehalose solution per each strip. The strips were inserted into small 2 cm by 5 cm PETG trays, and the small trays were inserted into large PETG trays and lyophilized. Each large tray accommodates 24 strips.

TABLE 1a

Stability of Healos ® with trehalose (250 mg) plus rhGDF-5 (2.5 mg) per strip at 25° C. (Example 1)

| Test | Parameter | 0 months | 0 months | 3 months | 6 months | 9 months | 12 months |
|---|---|---|---|---|---|---|---|
| RP-HPLC | % main peak | 89.54 | 82.26 | 81.49 | 77.98 | 76.57 | 72.19 |
| RP-HPLC | % aggregates | 0.00 | 3.01 | 5.08 | 4.53 | 5.40 | 6.60 |

TABLE 1b

Stability of Healos ® with trehalose (250 mg) plus rhGDF-5 (2.5 mg) per strip at 2-8° C. (Example 1)

| Test | Parameter | 0 months | 0 months | 3 months | 6 months | 9 months | 12 months |
|---|---|---|---|---|---|---|---|
| RP-HPLC | % main peak | 89.54 | 88.22 | 90.84 | 85.45 | 88.70 | 87.61 |
| RP-HPLC | % aggregates | 0.00 | 0.00 | 0.00 | 0.00 | 0.00 | 0.00 |

Example 2

Healos® strips (non-sterile) with rhGDF-5 (0.5 mg/ml, 5 ml/strip) and mannitol 50 mg/ml. Each strip had 2.5 mg of rhGDF-5 and 250 mg of mannitol.

Preparation of Mannitol Solution:

23.03 g of mannitol was carefully weighed and transferred into a sterile polypropylene bottle, to which 350 ml of purified water was added at room temperature and stirred slowly until a clear solution was obtained. The pH was measured and found to be 7.2; 0.1 N HCl was added drop by drop to adjust the pH to 3.8; then the volume was adjusted with purified water to obtain 400 ml final volume. The pH was measured and found to be 3.9. The solution was filtered through a 0.22-micron filter and was used directly to dilute the protein solution.

Dilution of rhGDF-5 Solution with Mannitol Solution:

22.37 ml of rhGDF-5 solution was carefully transferred to a polypropylene flask, to which mannitol solution was carefully added to adjust the volume to 150 ml. The pH was measured and found to be 2.7. The solution was stirred for 15 minutes at room temperature. The UV extinction coefficient was obtained to calculate an accurate protein concentration. Based on the UV reading, more mannitol solution was added to obtain the desired concentration of 0.5 mg/ml in 170 ml of solution; the pH was measured and found to be 2.8; the UV reading indicated 0.493 mg/ml protein content.

The rhGDF-5/mannitol solution was filtered through a 0.22-micron filter and was used directly to dispense onto Healos® strips. Using sterile pipettes, 2.5 ml of rhGDF-5/mannitol solution was dispensed onto strips equally at 2 spots for a total of 5 ml of rhGDF-5/mannitol solution per each strip. The strips were inserted into small 2 cm by 5 cm PETG trays, and the small trays were inserted in large PETG trays and lyophilized. Each large tray accommodates 24 strips.

TABLE 2a

Stability of Healos ® with mannitol (250 mg) plus rhGDF-5 (2.5 mg) per strip at 25° C. (Example 2)

| Test | Parameter | 0 months | 1 month | 3 months | 6 months | 9 months | 12 months |
|---|---|---|---|---|---|---|---|
| RP-HPLC | % main peak | 89.54 | 78.89 | 63.10 | 51.48 | At six months, the main peak was markedly decreased and accumulation of aggregates was increased. The stability studies were terminated at six months. | |
| RP-HPLC | % aggregate | 0.00 | 5.67 | 12.24 | 12.56 | | |

TABLE 2b

Stability of Healos ® with mannitol (250 mg) plus rhGDF-5 (2.5 mg) per strip at 2-8° C. (Example 2)

| Test | Parameter | 0 months | 1 month | 3 months | 6 months | 9 months | 12 months |
|---|---|---|---|---|---|---|---|
| RP-HPLC | % main peak | 89.71 | 89.12 | 86.26 | 81.02 | 82.97 | 79.78 |
| RP-HPLC | % aggregates | 0.00 | 0.00 | 2.70 | 3.21 | 4.01 | 4.12 |

Example 3

Healos® strips (sterile) with rhGDF-5 (0.5 mg/ml, 5 ml/strip) and trehalose 100 mg/ml. Each strip had 2.5 mg of rhGDF-5 and 500 mg of trehalose.
Preparation of Trehalose Solution:

25.49 g of trehalose dihydrate was carefully weighed and transferred into a sterile polypropylene bottle, to which 190 ml of purified water was added at room temperature and stirred slowly until a clear solution was obtained. The clear trehalose solution pH was measured and found to be 6.2. HCl was not added to the trehalose solution to adjust the pH. The volume was adjusted with purified water to obtain 200 ml final volume. The pH was measured and found to be 6.3. The solution was used directly to dilute the protein solution.
Dilution of rhGDF-5 Solution with Trehalose Solution:

23.03 ml of rhGDF-5 solution was carefully transferred to a polypropylene flask, to which trehalose solution was added carefully to adjust the volume to 170 ml. The pH was measured and found to be 3.0. The solution was stirred for 15 minutes at room temperature. The UV extinction coefficient was obtained to accurately calculate the protein concentration. Based on the UV reading, more trehalose solution was added to obtain the desired concentration of 0.5 mg/ml in 175 ml of solution; the pH was measured and found to be 3.0; the UV reading indicated 0.518 mg/ml protein concentration.

The rhGDF-5/trehalose solution was filtered through a 0.22-micron filter and was used directly to dispense onto sterile Healos® strips. Using sterile pipettes, 2.5 ml of rhGDF-5/trehalose solution was dispensed onto strips equally at 2 spots for a total of 5 ml of rhGDF-5/trehalose solution per each strip. The strips were placed on steel trays, which were carefully packed into sterile double pouches and transferred for lyophilization under sterile conditions.

TABLE 3a

Stability of Healos ® with trehalose (500 mg)/rhGDF-5 (2.5 mg) per strip at 2-8° C. (Example 3)

| Test | Parameter | 0 months | 1 month | 3 months | 6 months |
|---|---|---|---|---|---|
| RP-HPLC | % main peak | 88.5 | 83.9 | 90.0 | 78.9 |
| RP-HPLC | % aggregates | 0.0 | 0.0 | 0.0 | 0.0 |

Example 4

Healos® strips (sterile) with low dose rhGDF-5 (5 ml/strip, 0.5 mg/ml), trehalose 40 mg/ml and glycine 10 mg/ml. Each strip had 2.5 mg of rhGDF-5, 200 mg of trehalose and 50 mg of glycine.
Preparation of Trehalose/Glycine Solution:

17.84 g of trehalose dihydrate and 4.03 g of glycine were carefully weighed and transferred into a sterile polypropylene bottle, to which 300 ml of purified water was added at room temperature and stirred slowly until a clear solution was obtained. The pH was measured and found to be 5.5. Without adding any acid, the volume was adjusted to 350 ml with purified water. The pH was measured and found to be 5.5.
Dilution of rhGDF-5 Solution with Trehalose/glycine Solution:

39.47 ml of rhGDF-5 solution was carefully transferred to a polypropylene flask, to which trehalose/glycine solution was added carefully to adjust the volume to 295 ml. The pH was measured and found to be 4.1. The solution was stirred for 15 minutes at room temperature. The UV extinction coefficient was obtained to accurately calculate the protein concentration. Based on the UV reading, more trehalose solution was added to obtain the desired concentration of 0.5 mg/ml in 300 ml of solution; the pH was measured and found to be 4.1; the UV reading indicated 0.507 mg/ml protein concentration.

The solution was filtered through a 0.22-micron filter, and the solution was used directly to dispense on sterile Healos® strips. Using sterile pipettes, 2.5 ml of rhGDF-5/trehalose/glycine solution was dispensed onto strips equally at 2 spots for a total of 5 ml of rhGDF-5 solution per each strip. The strips were placed on steel trays, which were carefully packed into sterile double pouches and transferred for lyophilization under sterile conditions.

TABLE 4a

Stability of Healos ® with trehalose (200 mg)/rhGDF-5 (2.5 mg)/Glycine (50 mg) per strip at 2-8° C. (Example 4)

| Test | Parameter | 0 months | 1 month | 3 months | 6 months |
|---|---|---|---|---|---|
| RP-HPLC | % main peak | 87.9 | 83.5 | 86.0 | 80.1 |
| RP-HPLC | % aggregates | 0.0 | 0.0 | 0.0 | 0.0 |

TABLE 4b

Stability of Healos ® with trehalose (200 mg)/rhGDF-5 (2.5 mg)/Glycine (50 mg) per strip at 25° C. (Example 4)

| Test | Parameter | 0 months | 1 month | 3 months | 6 months |
|---|---|---|---|---|---|
| RP-HPLC | % main peak | 87.9 | 78.7 | 78.1 | 67.7 |
| RP-HPLC | % aggregates | 0.00 | 0.00 | 0.00 | 0.00 |

Example 5

Healos® strips (sterile) with rhGDF-5 (0.5 mg/ml, 2.5 mg/strip), trehalose 40 mg/ml, glycine 10 mg/ml and polysorbate 0.1 mg/ml. Each strip had 2.5 mg of rhGDF-5, 200 mg of trehalose, 50 mg of glycine and 0.5 mg of polysorbate 80.
Preparation of Polysorbate 80 Solution:

23.03 mg of polysorbate 80 was weighed into a 50 ml sterile disposable tube, to which 25 ml of purified water was added and vortexed for 2 minutes to obtain a homogenous solution.
Preparation of Trehalose/glycine/polysorbate Solution:

10.19 g of trehalose dihydrate and 2.303 g of glycine were carefully weighed and transferred into a sterile polypropylene bottle, to which the 25 ml polysorbate 80 solution from above was added. The polysorbate tube was rinsed 2 times with 25 ml of purified water and the rinses transferred to the trehalose/glycine/polysorbate solution. An additional amount of purified water was added to the trehalose/glycine/polysorbate solution for a total volume of 190 ml. The solution was stirred for 2 minutes to obtain a clear solution. The pH of the solution was measured and found to be 5.6; the volume was adjusted to 200 ml with purified water. The pH was measured and found to be 5.5.

Dilution of rhGDF-5 Solution with Trehalose/glycine/polysorbate Solution:

23.03 ml of rhGDF-5 solution was carefully transferred to a polypropylene flask, to which the trehalose/glycine/polysorbate solution was added carefully to adjust the volume to 170 ml. The pH was measured and found to be 4.1. The solution was stirred for 15 minutes at room temperature. The UV extinction coefficient was obtained to accurately calculate the protein concentration. Based on the UV reading, more trehalose/glycine/polysorbate solution was added to obtain the desired concentration of 0.5 mg/ml in 175 ml of solution; the pH was measured and found to be 4.1; the UV reading indicated 0.510 mg/ml protein concentration.

The solution was filtered through a 0.22-micron filter was used directly to dispense onto sterile Healos® strips in a laminar flow hood under aseptic conditions. Using sterile pipettes, 2.5 ml of rhGDF-5/trehalose/glycine/polysorbate solution was dispensed onto strips equally at 2 spots for a total of 5 ml of rhGDF-5/trehalose/glycine/polysorbate solution per each strip. The strips were placed on steel trays, which were carefully packed into sterile double pouches and transferred for lyophilization under sterile conditions.

TABLE 5a

Stability of Healos ® with trehalose (200 mg)/rhGDF-5 (2.5 mg)/Glycine (50 mg)/Polysorbate 80 (0.5 mg) per strip at 2-8° C. (Example 4)

| Test | Parameter | 0 months | 1 month | 3 months | 6 months |
|---|---|---|---|---|---|
| RP-HPLC | % main peak | 88.4 | 84.3 | 86.8 | 82.2 |
| RP-HPLC | % aggregates | 0.0 | 0.0 | 0.0 | 0.0 |

Example 6

Lyophilized vial product of rhGDF-5 (0.5 mg/ml) plus trehalose (50 mg/ml)

Preparation of Trehalose Solution:

A sterile polypropylene bottle was charged with 12.16 g of trehalose dihydrate and magnetic stir bar, to which 190 ml of purified water was added at room temperature. The solution was stirred at room temperature until the trehalose was completely dissolved. The pH was measured and found to be 6.5. To the clear trehalose solution, 0.1 N HCl was added drop by drop to adjust the pH to 5.8. The volume was adjusted to 200 ml with purified water; the pH was measured and found to be 5.5. The solution was filtered through 0.22-micron filter and was used directly to dilute the protein solution.

Dilution of rhGDF-5 Solution with Trehalose Solution:

14.47 ml of rhGDF-5 solution was carefully transferred to a polypropylene flask, to which trehalose solution was slowly added to a final volume of 100 ml while swirling the bottle. The solution was swirled occasionally at room temperature for 15 minutes; the pH was measured and found to be 3.0. Based on the UV reading, more trehalose solution was added to obtain the desired concentration of 0.5 mg/ml in 110 ml of solution; the pH was measured and found to be 3.1; the UV reading indicated 0.510 mg/ml protein concentration. The solution was filtered through a 0.22-micron filter and was used directly to dispense into vials.

Filling vials: 1.1 ml of rhGDF-5/trehalose solution was dispensed manually into 5 ml Type 1 flint glass vials, and each vial was partly closed with a stopper prior to loading into the lyophilizer. After lyophilization, the stoppers were pressed and crimped. The product was obtained as white to off-white cake.

TABLE 6a

Stability of vial of rhGDF-5 (0.5 mg/ml) plus trehalose (50 mg/ml) at 2-8° C. (Example 6)

| Test | Parameter | 0 months | 1 month | 3 months | 6 months | 9 months | 12 months |
|---|---|---|---|---|---|---|---|
| Cake Appearance & Integrity | white to off-white; intact | white to off-white; intact | white to off-white; intact | white to off-white; intact | white to off-white; intact | white to off-white; intact | white to off-white; intact |
| Reconstitution Time, minutes | <2 min | 1.13 | 0.28 | 1.32 | 0.38 | 0.44 | 0.34 |
| pH of Reconstituted Solution | 2.0 to 3.5 | 3.0 | 2.5 | 2.8 | 2.8 | 2.9 | 2.9 |
| Protein Concentration | mg/ml | 0.49 | 0.46 | 0.46 | 0.48 | 0.47 | 0.45 |
| RP-HPLC | % main peak | 90.74 | 88.58 | 92.91 | 92.96 | 92.77 | 93.19 |
| RP-HPLC | % aggregates | 0.00 | 0.00 | 0.00 | 0.00 | 0.00 | 0.00 |

TABLE 6b

Stability of vial of rhGDF-5 (0.5 mg/ml) plus trehalose (50 mg/ml) at 25° C. (Example 6)

| Test | Parameter | 0 months | 1 month | 3 months | 6 months | 9 months | 12 months |
|---|---|---|---|---|---|---|---|
| Cake Appearance & Integrity | white to off-white; intact | white to off-white; intact | white to off-white; intact | white to off-white; intact | white to off-white; intact | white to off-white; intact | white to off-white; intact |

TABLE 6b-continued

Stability of vial of rhGDF-5 (0.5 mg/ml) plus trehalose (50 mg/ml) at 25° C. (Example 6)

| Test | Parameter | 0 months | 1 month | 3 months | 6 months | 9 months | 12 months |
|---|---|---|---|---|---|---|---|
| Reconstitution Time, minutes | <2 min | 1.13 | 0.26 | 1.44 | 0.38 | 0.52 | 0.33 |
| pH of Reconstituted solution | 2.0 to 3.5 | 3.0 | 2.5 | 2.8 | 2.9 | 2.8 | 2.9 |
| Protein Concentration | mg/ml | 0.49 | 0.46 | 0.46 | 0.47 | 0.45 | 0.45 |
| RP-HPLC % main peak | % main peak | 90.74 | 86.24 | 87.75 | 85.39 | 84.19 | 82.45 |
| RP-HPLC % aggregates | % aggregates | 0.00 | 0.00 | 0.00 | 0.00 | 0.00 | 0.00 |

Example 7

Lyophilized vial product of rhGDF-5 (0.5 mg/ml) plus mannitol (50 mg/ml)

Preparation of Mannitol Solution:

A sterile polypropylene bottle was charged with 11.52 g of mannitol and a magnetic stir bar, to which 185 ml of purified water was added at room temperature. The mixture was stirred for 10 minutes at room temperature until the mannitol was completely dissolved. The pH was measured and found to be 6.6. To the clear solution, 0.1 N HCl was added drop by drop to adjust the pH to 5.5. The volume was adjusted to 200 ml with purified water; the pH was measured and found to be 5.7. The solution was filtered through a 0.22-micron filter and was used directly to dilute the protein solution.

Dilution of rhGDF-5 Solution with Mannitol Solution:

To a polypropylene flask, 14.48 ml of rhGDF-5 solution was carefully transferred; to which the mannitol solution was added carefully to a volume of 100 ml. The solution was stirred for 15 minutes at room temperature. The UV extinction coefficient was obtained to accurately calculate the protein concentration. Based on the UV reading, more mannitol solution was added to obtain the desired protein concentration of 0.5 mg/ml in 110 ml of solution; the pH was measured and found to be 3.1; the UV reading indicated 0.498 mg/ml protein concentration. The solution was filtered through a 0.22-micron filter and was used directly to dispense into vials.

Filling vials: 1.1 ml of mannitol/rhGDF-5 solution was dispensed manually into 5 ml Type 1 flint glass vials, and each vial was partly closed with a stopper prior to loading into the lyophilizer. After lyophilization, the stoppers were pressed and crimped. The product was obtained as white to off-white cake.

TABLE 7a

Stability of vial of rhGDF-5 (0.5 mg/ml) plus mannitol (50 mg/ml) at 2-8° C. (Example 7)

| Test | Parameter | 0 months | 1 month | 3 months | 6 months | 9 months | 12 months |
|---|---|---|---|---|---|---|---|
| Cake Appearance & Integrity | white to off-white; intact | white to off-white; intact | white to off-white; intact | white to off-white; intact | white to off-white; intact | | The stability data at 6 months were not promising as evidenced by the decrease in the main peak and the increase in aggregates, hence the stability studies were terminated at 6 months. |
| Reconstitution Time, minutes | <2 min | | 0.95 | 0.26 | 0.39 | 0.22 | |
| pH of Reconstituted Solution | 2.0 to 4.0 | | 3.5 | 3.2 | 3.3 | 3.9 | |
| Protein Concentration | mg/ml | | 0.41 | 0.39 | 0.37 | 0.36 | |
| RP-HPLC | % main peak | 89.85 | 86.65 | 82.04 | 53.59 | | |
| RP-HPLC | % aggregates | 0.00 | 0.00 | 4.3 | 7.82 | | |

TABLE 7b

Stability of vial of rhGDF-5 (0.5 mg/ml) plus mannitol (50 mg/ml) at 25° C. (Example 7)

| Test | Parameter | 0 months | 1 month | 3 months | 6 months | 9 months | 12 months |
|---|---|---|---|---|---|---|---|
| Cake Appearance & Integrity | white to off-white; intact | white to off-white; intact | white to off-white; intact | white to off-white; intact | white to off-white; intact | | The stability data at 6 months were not promising, |

TABLE 7b-continued

Stability of vial of rhGDF-5 (0.5 mg/ml) plus
mannitol (50 mg/ml) at 25° C. (Example 7)

| Test | Parameter | 0 months | 1 month | 3 months | 6 months | 9 months | 12 months |
|---|---|---|---|---|---|---|---|
| Reconstitution time, minutes | <2 min | 0.95 | 0.35 | 0.35 | 0.28 | hence the stability studies were terminated at 6 months. | |
| pH of Reconstituted solution | 2.0 to 4.0 | 3.5 | 3.4 | 3.6 | 4.0 | | |
| Protein Concentration | mg/ml | 0.41 | 0.32 | 0.28 | 0.26 | | |
| RP-HPLC | % main peak | 89.85 | 34.31 | 26.04 | 34.62 | | |
| RP-HPLC | % aggregates | 0.00 | 7.05 | 14.21 | 17.30 | | |

Example 8

Lyophilized vial product of rhGDF-5 (0.5 mg/ml) plus trehalose (50 mg/ml) in glycine-HCl pH 3.0 buffer.
Preparation of Trehalose Solution:
A sterile polypropylene bottle was charged with 12.16 g of trehalose dihydrate and a magnetic stir bar, to which 200 ml of 5 mM glycine-HCl buffer pH 3.0 was added at room temperature. The solution was stirred at room temperature until the trehalose was completely dissolved. The pH of trehalose/glycine solution was 3.1. The solution was filtered through 0.22-micron filter and was used directly to dilute the protein solution.
Dilution of rhGDF-5 Solution with Trehalose Solution:
Bulk rhGDF-5 solution was dialyzed against a 5 mM glycine-HCl buffer over night using a 3000 M.W. cut-off membrane at 2-8° C. After dialysis the solution was slightly concentrated to 3.8 mg/ml. 14.47 ml of rhGDF-5 solution was carefully transferred to a polypropylene flask, to which trehalose-glycine solution was slowly added to a final volume of 100 ml while swirling the bottle. The solution was swirled occasionally at room temperature for 15 minutes; the pH was measured and found to be 3.0. Based on the UV reading, more trehalose-glycine solution was added to obtain the desired protein concentration of 0.5 mg/ml in 110 ml of solution; the pH was measured and found to be 3.0; the UV reading indicated 0.507 mg/ml protein concentration. The solution was filtered through a 0.22-micron filter and was used directly to dispense into vials.
Filling vials: 1.1 ml of rhGDF-5/trehalose solution was dispensed manually into 5 ml Type 1 flint glass vials, and each vial was partly closed with a stopper prior to loading into the lyophilizer. After lyophilization, the stoppers were pressed and crimped. The product was obtained as white to off-white cake.

TABLE 8

Stability of vial of rhGDF-5 (0.5 mg/ml) plus trehalose (50 mg/ml) in
glycine-HCl buffer pH 3.0 (Example 8)

| Time and Temperature | Cake appearance | Solution appearance after reconstitution | Protein main peak % recovery HPLC | % aggregates HPLC |
|---|---|---|---|---|
| Time = zero | Solid, white-to off-white, | clear | 100 | 0 |
| 1 month, 50 C. | Solid, white to off-white | clear | 100 | 0 |
| 2 month, 50 C. | Solid, white to off-white | clear | 99.6 | 0 |
| 3 month, 50 C. | Solid, white to off-white | clear | 100 | 0 |
| 1 month, 250 C. | Solid, white to off-white | clear | 100 | 0 |
| 2 month, 250 C. | Solid, white to off-white | clear | 99.0 | 0 |
| 3 month, 250 C. | Solid, white to off-white | clear | 99.3 | 0 |
| 1 month, 400 C. | Solid, white to off-white | clear | 98.7 | 0 |
| 2 month, 400 C. | Solid, white to off-white | clear | 99.1 | 0 |
| 3 month, 400 C. | Solid, white to off-white | clear | 98.9 | 0 |

Example 9

Lyophilized vial product of rhGDF-5 (0.5 mg/ml) plus trehalose (50 mg/ml) in phosphate buffer at pH 3.0.
Preparation of Trehalose Solution:
A sterile polypropylene bottle was charged with 12.16 g of trehalose dihydrate and a magnetic stir bar, to which 200 ml of 5 mM phosphate buffer pH 3.0 was added at room temperature. The solution was stirred at room temperature until the trehalose was completely dissolved. The pH of the trehalose/phosphate buffer solution was 3.0. The solution was filtered through a 0.22-micron filter and was used directly to dilute the protein solution.
Dilution of rhGDF-5 Solution with Trehalose Solution:
Bulk rhGDF-5 solution was dialyzed against phosphate buffer over night using a 3000 M.W. cut-off membrane at 2-8° C. After dialysis the solution was slightly concentrated to 3.8 mg/ml. 14.47 ml of rhGDF-5 solution was carefully transferred to a polypropylene flask, to which trehalose/phosphate buffer solution was slowly added to a final volume of 100 ml while swirling the bottle. The solution was swirled occasionally at room temperature for 15 minutes; the pH was measured and found to be 3.0. Based on the UV reading, more trehalose/phosphate buffer solution was added to obtain the desired protein concentration of 0.5 mg/ml in 110 ml of solution; the pH was measured and found to be 3.0; the UV reading indicated 0.50 mg/ml protein concentration. The solution was filtered through a 0.22-micron filter and was used directly to dispense into vials.

Filling vials: 1.1 ml of rhGDF-5/trehalose solution was dispensed manually into 5 ml Type 1 flint glass vials, and each vial was partly closed with a stopper prior to loading into the lyophilizer. After lyophilization, the stoppers were pressed and crimped. The product was obtained as white to off-white cake.

TABLE 9

Stability of rhGDF-5 (0.5 mg/ml) plus trehalose (50 mg/ml) in phosphate buffer at pH 3.0 (Example 9)

| Time and Temperature | Cake appearance | Solution appearance after reconstitution | Protein main peak % recovery HPLC | % aggregates HPLC |
|---|---|---|---|---|
| Time = zero | Solid, white- to off-white, | clear | 100 | 0 |
| 1 month, 50 C. | Solid, white to off-white | clear | 100 | 0 |
| 2 month, 50 C. | Solid, white to off-white | clear | 99.8 | 0 |
| 3 month, 50 C. | Solid, white to off-white | clear | 100 | 0 |
| 1 month, 250 C. | Solid, white to off-white | clear | 100 | 0 |
| 2 month, 250 C. | Solid, white to off-white | clear | 98.7 | 0 |
| 3 month, 250 C. | Solid, white to off-white | clear | 99.7 | 0 |
| 1 month, 400 C. | Solid, white to off-white | clear | 98.7 | 0 |
| 2 month, 400 C. | Solid, white to off-white | clear | 97.4 | 0 |
| 3 month, 400 C. | Solid, white to off-white | clear | 97.4 | 0 |

Example 10

Morselized collagen cylinder with 2.5 mg rhGDF-5 and 250 mg trehalose

Preparation of Trehalose Solution:

9.56 g of trehalose dihydrate was carefully weighed and transferred into a sterile polypropylene bottle, to which 145 ml of purified water was added at room temperature and stirred slowly until a clear solution was obtained. The clear trehalose solution pH was measured and found to be 5.3. The volume was adjusted with purified water to obtain 150 ml final volume. The pH of the solution was measured and found to be 5.3. The solution was used directly to dilute the protein solution.

Dilution of rhGDF-5 Solution with Trehalose Solution:

16.45 ml of rhGDF-5 solution was carefully transferred to a polypropylene flask, to which trehalose solution was added carefully to adjust the volume to 120 ml; the pH was measured and found to be 2.9. The solution was stirred for 15 minutes at room temperature. The UV extinction coefficient was obtained to accurately calculate the protein concentration. Based on the UV reading, more trehalose solution was added to obtain the desired protein concentration of 0.5 mg/ml in 125 ml of solution; the pH was measured and found to be 2.9; the UV reading indicated 0.498 mg/ml protein concentration.

Dosing of Morselized Collagen Cylinders with rhGDF-5/Trehalose Solution

The solution was filtered through a 0.22-micron filter and the solution was used directly to dispense on pre-formed morselized collagen cylinders that were packed in a Teflon mold. Each cylinder was dosed with 5 ml of rhGDF-5/trehalose solution prior to lyophilization.

TABLE 10

Stability of morselized collagen cylinder with rhGDF-5 (2.5 mg) and trehalose (250 mg) per cylinder at 2-8° C. (Example 10)

| Test | Parameter | 0 months | 1 month | 3 months | 6 months | 9 months | 12 months |
|---|---|---|---|---|---|---|---|
| RP-HPLC | % main peak | 87.28 | 87.29 | 86.67 | 90.01 | Study in progress | |
| RP-HPLC | % aggregates | 0.0 | 0 | 0 | 0 | | |

The data below in table 11 show that the rhGDF-5 without any excipients and deposited onto Healos® and lyophilized is stable at −20° C., but not at 2-8° C., as evidenced by the appearance of a late eluting peak in the RP-HPLC test of the 2-8° C. samples, but not the −20° C. samples.

TABLE 11

Stability of Healos ® strip with 5 ml of rhGDF-5 (0.5 mg/ml) without excipients at 2-8° C. and at −20° C.

| Test | Parameter: % Late Eluting Peak | 0 months | 1 month | 2 months | 6 months | 9 months | 12 months | 18 months |
|---|---|---|---|---|---|---|---|---|
| RP-HPLC | 2-8° C. | 0 | 9.0 | 12.8 | 36.5 | 45.9 | 49.0 | 42.1 |
| RP-HPLC | −20° C. | 0 | 2.6 | 0 | 1.6 | 2.2 | 2.7 | 3.8 |

Different examples of making flowable morselized collagen/rhGDF-5 with excipients and soluble collagen gel have been developed, and each example was evaluated for its performance, stability, and ease of manufacturing.

Morselized Collagen Example 1:
  Morselized collagen cylinder & rhGDF-5 lyophilized in the dry form
  Collagen gel in wet form is kept separate
  Both are kept separately in separate syringes at 2-8° C.
  Both are mixed prior to injection Morselized Collagen Example 2:
  Morselized collagen cylinder & rhGDF-5 & collagen gel mixed together in wet form (not lyophilized)
  All are kept in a single syringe in wet form at 2-8° C.; ready to use Morselized Collagen Example 3:
  Morselized collagen cylinder & rhGDF-5 & collagen gel lyophilized in the dry form
    all are kept in dry form in a single syringe at 2-8° C.
    rehydrate with water prior to injection Morselized Collagen Example 4:
  Morselized collagen cylinder & collagen gel together as a paste
  rhGDF-5 is kept separate in dry form
  Both are kept separately in separate syringes at 2-8° C.
  Both are mixed prior to injection Morselized Collagen Example 5:
  Morselized collagen cylinder & collagen gel together in dry form
  rhGDF-5 is kept separate in dry form
  Both are kept separately in separate syringes at 2-8° C.
  Reconstitute the rhGDF-5 with sterile water or bone marrow aspirate
  Dry morselized collagen and collagen are mixed with reconstituted rhGDF-5 solution prior to injection The stability of rhGDF-5 was assessed using the following techniques: RP-HPLC, differential scanning calorimetry (DSC), circular dichroism (CD), polarized light microscopy (PLM), and also bioassay, with several excipients such as mannitol, sucrose, and trehalose in the presence and absence of buffers and anti-oxidants. Several sucrose-containing lyophilized formulations of rhGDF-5 developed an undesirable yellow color and glassy cake structure during storage and therefore were not promising.

The melting behavior of lyophilized rhGDF-5 formulations was studied using DSC. The DSC data demonstrated that both trehalose and mannitol-based formulations significantly improved the thermal stability of bulk rhGDF-5.

FIGS. 1, 2 and 3 show a comparison of the DSC profiles of the trehalose formulation and mannitol formulation of rhGDF-5 compared to that of bulk rhGDF-5. Bulk rhGDF-5 displays two major transitions: one near 40° C. and the other near 85° C. The high temperature transition probably represents the protein's thermal unfolding. It is interesting to note that the melting temperature ($T_m$) of the first endothermic transition is increased by 7-14° C. in the presence of excipients. When considered by itself, this study suggests that both trehalose and mannitol could be equally effective as a stabilizer.

PLM (polarized light microscopy) of the trehalose/rhGDF-5 formulation is shown in FIG. 4. The sample does not show a major birefringence phenomenon. Thus, the system is amorphous, which is ideal for therapeutic applications. FIG. 5 shows the PLM of the mannitol/rhGDF-5 formulation after a period of storage. Many crystals were observed in the sample, indicating that the mannitol had crystallized during storage. This result suggests that trehalose is the better lyoprotectant for rhGDF-5. The far UV CD spectra revealed that trehalose-based formulations have a secondary structural distribution comparable to that of native bulk protein.

Real time stability studies by RP-HPLC of lyophilized rhGDF-5 with various excipients clearly demonstrated that rhGDF-5 in the presence of trehalose, at either 50 mg/ml or 100 mg/ml concentrations, with or without buffers, and with or without polysorbate, consistently imparted improved stability upon rhGDF-5 at both 2-8° C. and 15-25° C. storage conditions, whereas mannitol failed to provide the same level of stability under similar storage conditions.

The real time stability studies of lyophilized cake formulations clearly showed that mannitol did not stabilize the protein, as evidenced by the main peak being decreased significantly while the aggregate peak is increased at room temperature, as well as 2-8° C. storage conditions. The aggregates are the most undesirable species in the protein formulations as they may cause immunological reactions and side effects. In contrast, trehalose stabilized the protein very well by inhibiting the formation of aggregates and protecting the main peak, particularly at 2-8° C. storage conditions, as evidenced in real time stability studies. Thus trehalose is better than mannitol in stabilizing rhGDF-5 in formulations. Also, the real time stability data indicate that rhGDF-5/trehalose formulations having phosphate or glycine as a buffer to control the pH is even better than rhGDF-5/trehalose formulations without buffers. The real time stability data indicate that the ideal storage of rhGDF-5 trehalose/glycine formulations is at 2-8° C., and also that storage at 25° C. is adequate.

In addition to the favorable biochemical and biophysical data of trehalose-based rhGDF-5 formulations, these formulations also showed potency in the alkaline phosphatase biological assay. Physical chemical methods of analysis, in vitro assays, and real time stability data show the promise of trehalose as a superior excipient in stabilizing rhGDF-5 in a lyophilized stand-alone product, as well as collagen-based combination products for use in the treatment of a variety of musculoskeletal disorders.

Example 11

Solubility of rhGDF-5 in Different Ionic Strength Solutions and Two pH Buffers (pH 3 and pH 4)

Various ionic strength solutions of sodium phosphate buffer were used in this study. A bulk protein solution was concentrated to approximately 10 mg/mL and dialyzed with 5, 10, 25, 50 and 100 mM phosphate buffers at pH 3 or pH 4. After dialysis, the samples were checked for clarity and analyzed for protein concentration on an UV-Vis spectrophotometer. Detailed procedures are described below.

Buffer Preparations
  100 mM Phosphate Buffer at pH 3:
    13.5 mL of concentrated $H_3PO_4$ (14.8 M) solution was transferred to a 2000-mL beaker, to which DI water was added up to 1900-mL mark. The solution was titrated with a NaOH solution to pH 3 and transferred to a 2000-mL graduated cylinder. Additional water was added to make up 2000 mL. The content was transferred back to the beaker and mixed thoroughly.
  50 mM Phosphate Buffer at pH 3:
    6.76 mL of concentrated $H_3PO_4$ (14.8 M) solution was transferred to a 2000-mL beaker, to which DI water was added up to 1900-mL mark. The solution was titrated with a NaOH solution to pH 3 and transferred to a 2000-mL graduated cylinder. Additional water was added to make up 2000 mL. The content was transferred back to the beaker and mixed thoroughly.

25 mM Phosphate Buffer at pH 3:

3.39 mL of concentrated H3PO4 (14.8 M) solution was transferred to a 2000-mL beaker followed by addition of DI water to 1900-mL mark. The solution was titrated with a NaOH solution to pH 3 and transferred to a 2000-mL graduated cylinder. Additional water was added to make up 2000 mL. The content was transferred back to the beaker and mixed thoroughly.

10 mM Phosphate Buffer at pH 3:

1.35 mL of concentrated $H_3PO_4$ (14.8 M) solution was transferred to a 2000-mL beaker to which DI water was added up to 1900-mL mark. The solution was titrated with a NaOH solution to pH 3 and transferred to a 2000-mL graduated cylinder. Additional water was added to make up 2000 mL. The content was transferred back to the beaker and mixed thoroughly.

5 mM Phosphate Buffer at pH 3:

0.676 mL of concentrated $H_3PO_4$ (14.8 M) was transferred to a 2000-mL beaker followed by addition of DI water to 1900-mL mark. The solution was titrated with a NaOH solution to pH 3 and transferred to a 2000-mL graduated cylinder. Additional water was added to make up 2000 mL. The content was transferred back to the beaker and mixed thoroughly.

Sample Preparation

Bulk protein rhGDF-5 (Lot # 2142131) was thawed at 2-8° C. The bulk protein solution (24 mL at 3.8 mg/mL) was concentrated using a centrifugal filtration device (Pall Life Science, Cat # OD010C37, 10K MWCO) to a volume of approximately 6 mL. Approximately 0.9 mL of the concentrated rhGDF-5 solution was transferred to each dialysis cassette (Pierce, Cat # 66380) and dialyzed against the phosphate buffers over night at room temperature. The concentrated rhGDF-5 solutions were carefully removed from the dialysis cassettes and placed in small glass vials to check solution clarity. Protein concentrations were determined on an UV-Vis spectrophotometer as described in the Analytical Methods section.

Solubility at pH 4

Buffers of pH 4.0 were prepared from the pH 3 buffers by adding more NaOH solution to the pH 3 buffers. The protein solutions were dialyzed against the pH 4 buffers at room temperature over night. The samples were analyzed for solution clarity and protein concentration.

Analytical Methods

Solution samples in small glass vials were checked for clarity and particles. The sample vials were inspected using a vertical light against a black background. The clarity of the test samples was compared with a pure water sample as a control. The pH of each solution sample was measured directly using a calibrated pH meter.

Results

The results of the solubility study of 10 mg/ml rhGDF-5 solutions showed that the lower ionic strength buffers of sodium phosphate at 5, 10, and 25 mM yielded clear solutions, indicating good solubility, while higher ionic strength buffers of sodium phosphate at 50 and 100 mM yielded hazy solutions, indicating poor solubility. At pH 4, the 5 and 10 mM sodium phosphate buffers yielded hazy solutions, indicating poor solubility. Sodium phosphate buffers at 25, 50 and 100 mM yielded clear solutions after centrifugation, but had nearly zero protein recovery, indicating that the protein had precipitated. Thus, low ionic strength buffers near pH 3 would be preferable to higher ionic strength buffers at higher pH.

Example 12

Stability of rhGDF-5 at Various Temperatures in Various Buffers with 5% Trehalose In this study various buffers were tested for their effects on protecting 0.7 mg/mL rhGDF-5 in a 5% trehalose solution during lyophilization and storage at 5° C. The buffers tested were 5 mM glycine-HCl pH3, 5 mM sodium phosphate pH 3, 5 mM sodium citrate pH 3, 10 mM sodium lactate pH 3, 0.01% TFA in water, 1 mM HCl, and a control solution of rhGDF-5 in 1 mM HCl with no trehalose present. The buffers were prepared as follows:

5 mM Glycine Buffer, pH 3

A 2000-mL beaker was charged with 0.75 g of glycine (MW 75.05 g) and 1900 ml of DI water; the solution was titrated with a HCl solution to pH 3 while it was stirring. Additional water was added to make up 2000 mL and mixed thoroughly.

5 mM Citrate Buffer, pH 3

A 2000-mL beaker was charged with 2.11 g of citric acid monohydrate (MW210.14) and 1900 ml of DI water; the solution was titrated with a NaOH solution to pH 3. Additional water was added to make up 2000 mL and the solution was mixed.

5 mM Phosphate Buffer, pH 3

0.676 mL phosphoric acid solution (14.8M) was transferred to a 2000-mL beaker containing 1900 mL of DI water; the solution was titrated with a NaOH solution to pH 3. Additional water was added to make up 2000 mL and the solution was mixed thoroughly.

10 mM Lactate Buffer, pH 3

A 2000-ml size beaker was charged with 1.81 g lactic acid (MW 90.08) and 1900 ml of DI water; the resulted solution was titrated with a NaOH solution to pH 3. Additional water was added to make 2000 mL and the solution was mixed thoroughly.

1 mM HCl Solution 1 mL of 2N HCl solution was transferred to a 2000-mL beaker containing 1900 ml of DI water. Final volume of the solution was adjusted to 2000 mL mark by adding more DI water.

0.01% TFA Solution 0.2 mL TFA solution was transferred to a 2000-mL beaker containing 1900 ml of DI water. Final volume of the solution was adjusted to 2000 mL by adding additional water and the solution was mixed thoroughly.

Formulation Preparation

Bulk protein rhGDF-5 (Lot # 2142131) was thawed at 2-8° C. The bulk protein solution (55 mL at 3.8 mg/mL) was concentrated using a centrifugal filtration device (Pall Life Science, Cat # OD010C37, 10K MWCO) to a volume of approximately 10 mL. Approximately 1.4 mL of concentrated rhGDF-5 solution was transferred to each dialysis cassette (Pierce, Cat # 66380) and the cassettes were dialyzed against the test buffers over night at 2-8° C.

The rhGDF-5 solutions were removed carefully from the dialysis cassettes and transferred to small glass bottles. Protein concentrations of the solutions were measured using an UV-Vis spectrophotometer. The protein was formulated at approximately 0.7 mg/mL with 5% (w/v) trehalose in the test buffers and filtered through 0.22 μm filters. The solutions were stored at 2-8° C. prior to lyophilization.

Filling and Lyophilization

Each formulated solution was filled into 3-mL glass vials (West Pharmaceutical Services, Cat # 68000316) at 1 mL/vial. The vials were close partially with stoppers (West Pharmaceutical Services, Cat # 99150630) and transferred to the lyophilizer (FTS System, LyoStar II). Thermocouples were placed in placebo vials to monitor the lyophilization process. As a control, another formulation with no trehalose was also tested. 200 µL of 4.5 mg/mL rhGDF-5 in 1 mM HCl solution was transferred to each glass vial and lyophilized.

Analytical Methods

Integrity of Lyophilization Cakes

The lyophilized sample was checked at each time point for cracks, shrinkage and collapse of lyophilized cakes.

Reconstitution Time

One milliliter of DI water was added to each lyophilized sample and mixed gently. The reconstitution time was recorded.

Solution Clarity—Visual Appearance

Solution samples in small glass vials were checked for clarity and particles. The sample vials were inspected using a vertical light against a black background. The clarity of the test samples was compared with a pure water sample as a control.

pH Method pH of each solution sample was measured directly using a calibrated pH meter.

UV Spectroscopy

Protein concentration was determined using an UV-Vis spectrophotometer. The concentration of rhGDF-5 was calculated using an extinction coefficient of 1.16 mL/mg*cm at 280 nm.

HPLC Method

The non-reduced rpHPLC method (TM 0051 D) was used to monitor modified species of the protein. The test samples were diluted with 50 mM acetic acid to approximately 0.1 mg rhGDF-5/mL solution. The diluted samples (50 µl each) were injected onto the HPLC column (Vydac 218TP52, C18 column). The samples were eluted with 0.15% (v/v) TFA in water and 0.15% (v/v) TFA in acetonitrile as the mobile phase at 0.3 ml/min. The eluted peaks were detected at 214 nm. Percentage of each peak area was calculated to monitor the changes of the main peak and minor peaks (degraded peaks).

Size Exclusion Chromatography (SEC)

Protein aggregation was monitored using a SEC method. Typically, 30 µL of each test sample was injected directly onto the SEC column (TOSOH Bioscience, Cat # 08540) and eluted with 0.1% (v/v) TFA and 45% (v/v) acetonitrile in water at a rate of 0.5 ml/min. The protein peaks were monitored at 280 nm and the percentage of aggregate was calculated.

Gel Electrophoresis

Protein aggregates and degraded small pieces were also monitored using a gel electrophoresis method. Typically, approximately 10 µg protein was dried and reconstituted with 70 µL of SDS-PAGE sample buffer (Invitrogen, Cat # LC2676) with or without 10% β-mercaptoethanol. The samples were incubated at 95° C. for 5 minutes. Approximately 18 µL of each sample was loaded on to gels (Invitrogen, Cat # NP0341 Box). The gels were run using a running buffer (Invitrogen, Cat # NP0002) at 200 voltages for about 35 minutes. The gels were then stained with Simplyblue solution (Invitrogen, Cat # LC6060) and de-stained with DI water. The gels were scanned and images were collected.

Biological Activity Assay

Only the 6-month stability samples (glycine formulation and HCl formulation) were analyzed for biological activity. The cell-based assay (TM 0046) was used to measure alkaline phosphatase activity to determine the stability of the samples.

Water Content

The moisture content assay was conducted by PDD using a Karl Fischer Titration method.

Results

Integrity of Lyophilization Cakes

Test sample cakes in all storage conditions appeared solid and white to off-white from the time zero through the 9-month time point. Slight shrinkage was observed around the cakes, or the cakes were slightly separated from glass wall of the vials, as is commonly observed when sugars such as trehalose or sucrose are used as a bulking agent. There was no collapse of cake in all the test samples. Usually cake collapse may alter the reconstitution time and lead to protein instability. White, fluffy and light cakes were obtained in the formulation with no trehalose present.

Reconstitution Time

One milliliter of water was added to each sample vial at the time of testing. The sample was gently mixed and reconstitution time was recorded. Approximately 30 to 40 seconds were required for the completion of cake solubility.

Solution Clarity

Reconstituted solution samples were inspected under a vertical light on a black background; all sample solutions are found clear and colorless pH The pH of reconstituted solution was measured using a calibrated pH meter. Through out the course of study there were no significant changes in pH value across all the formulations. pH of the formulation samples containing trehalose/buffers was around 3.0±0.2. The pH of the formulation without trehalose was about 4.0.

UV Spectroscopy

The protein concentration was measured on an UV-VIS spectrophotometer. Through out the study there were no significant changes in protein concentration in rhGDF-5/trehalose formulations containing the glycine buffer, phosphate buffer, citrate buffer, lactate buffer, or 0.01% TFA. The absorbance at 280 nm was increased in the rhGDF-5/trehalose/HCl formulation when it was stored at 25° C./60% and 40° C./75% RH. The concentration of protein appeared to be increasing in the formulation that was stored at 40° C.; the initial protein concentration of 0.7 mg/mL at time zero was increased to 1 mg/mL at the 6-month time point. This may imply that trehalose might degrade to furfural compounds, which have similar absorbance at 280 nm.

Non-Reduced rpHPLC Results

The non-reduced rpHPLC method was used to monitor the degradation species of rhGDF-5, which were formed by methionine oxidation, deamidation reaction and other reactions. There were no significant changes in percentage of the main peak for all the formulations stored at 2-8° C. and 25° C. for 9 months, except for the HCl formulation and the formulation without trehalose. Both formulations had less than 90% of the main peak at the 9-month time point.

However, when the formulations were stored at accelerated storage conditions such as 40° C./75% RH, only one formulation (i.e. rhGF-5/trehalose/glycine) had greater than 91% of the main peak at the 6-month time point. The other formulations were not as stable as rhGDF-5/trehalose/glycine formulation under the accelerated storage conditions. Particularly, rhGDF-5/trehalose/HCl formulation had only 66% of the main peak at the 6-month time point. FIGS. 6 and 7 shows the HPLC chromatograms of rhGDF-5/trehalose/glycine formulation and rhGDF-5/trehalose/HCl formulation stored at 40°

C./75% RH for 6 months. FIGS. 8, 9, and 10 show the protein recovery of the various buffers tested at storage at 5°, 25°, and 40° C.

The results from rpHPLC analysis indicate that a combination of trehalose and glycine buffer provides the best stability to lyophilized rhGDF-5 during the storage. Additionally, the formulation of rhGDF-5/trehalose/HCl is less stable because the strong acid of HCl may have some destabilizing effects on both protein as well as trehalose.

Example 13

Stability of rhGDF-5 at Various Temperatures in a pH 3 Glycine Buffer with 5% Trehalose In this study, rhGDF-5 was formulated at approximately 0.01, 0.03, 0.1, 2.5, 4.5 and 9 mg/mL with 5% (w/v) trehalose and 5 mM glycine-HCl buffer at pH 3. The formulated solutions were used to fill in 3-mL glass vials at 1 mL/vial and the vials were lyophilized. The lyophilized sample vials were stored at 2-8° C., 25° C./60% RH and 40° C./75% RH. At each designated time point, the samples were analyzed for the stability of the products. The methods used in this study include cake appearance, reconstitution time, solution clarity, pH, rpHPLC (reverse phase high performance liquid chromatography), UV (ultra-violet spectroscopy), SEC (size exclusion chromatography) and gel electrophoresis. After 6-month storage at the three storage conditions, it was found that there were no significant changes observed in the formulations with protein concentrations from as low as 0.1 mg/ml to as high as 9 mg/mL. When the protein concentration was too low, such as 0.01 and 0.03 mg/ml, the existing methods were not robust enough to detect minor changes.

The results of this study indicate that lyophilized rhGDF-5 formulations containing trehalose and glycine-HCl with varying protein concentrations were stable at 2-8° C., 25° C./60% RH for at least 6 months. Slight changes in rpHPLC profile were seen in the product stored at accelerated storage conditions of 40° C./75% RH at the 6-month time point.

Example 14

Stability of Different Concentrations of rhGDF-5 at Various Temperatures in a pH 3 Glycine Buffer with 5% Trehalose In this study rhGDF-5 was formulated with 5% (v/w) trehalose and 5 mM glycine buffer at pH 3 with concentrations of rhGDF-5 of 0.01, 0.03, 0.1, 2.5, 4.5, and 9.0 mg/ml. Additionally, one formulation of 4.5 mg/ml rhGDF-5 was prepared with 10% (w/v) trehalose and 5 mM glycine buffer (pH 3) for comparison. The formulated solutions were then filled in 3-mL glass vials at 1 mL/vial and lyophilized. The lyophilized samples were stored in stability chambers.

5 mM Glycine-HCl Buffer, pH 3

3×0.75 g glycine (MW 75.07 g) was weighed into 3×2000-mL beakers and approximately 1900 mL of DI water was added to each beaker. The solutions were titrated with a HCl solution to pH 3. Additional water was added to the final volume of 2000 mL for each beaker and mixed thoroughly.

Formulation Preparation

Bulk protein rhGDF-5 (Lot # 2142131) was thawed at 2-8° C. The protein solution (96 mL at 3.8 mg/mL) was concentrated using 4 centrifugal filtration devices (Pall Life Science, Cat # OD010C37, 10K MWCO) to a total volume combined of approximately 24 mL. Approximately 3×8 mL of the concentrated rhGDF-5 solution was transferred to 3× dialysis cassettes (Pierce, Cat # 66380) and dialyzed against the glycine-HCl buffer over night at 2-8° C.

The rhGDF-5 solutions were transferred from the dialysis cassettes to a small glass bottle. Protein concentration was measured using an UV-Vis spectrophotometer. The protein was formulated at various concentrations with 5 or 10% (w/v) trehalose and 5 mM glycine buffer as described above. The formulated solutions were filtered with 0.22 μm filters and stored at 2-8° C. prior to lyophilization.

Fill and Lyophilization

Each of the formulated solutions was filled into 3-mL glass vials (West Pharmaceutical Services, Cat # 68000316) at 1 mL/vial. Stoppers (West Pharmaceutical Services, Cat # 99150630) were partially placed on the vials. The sample vials were transferred to the lyophilizer (FTS System, LyoStar II). Thermocouples were placed in placebo vials to monitor the temperature profiles during lyophilization process.

Analytical methods used were similar to those described above in examples 11 and 12.

Results

Integrity of Lyophilization Cakes

Test sample cakes in all storage conditions appeared solid and white from time zero through 6-month time point. Slight shrinkage was observed around the cakes or the cakes were slightly separated from glass wall of the vials. This is quite common when sugars, such as trehalose or sucrose are used as a bulking agent. No collapsed cakes were seen in all the test samples.

Reconstitution Time

One milliliter of water was added to each sample vial at the time points of testing. The vial was gently mixed and reconstitution time was recorded. It took approximately 30 to 40 seconds for the cake to go into solution.

Solution Clarity

All reconstituted samples appeared clear and colorless when the protein solutions were inspected with a vertical light against a black background.

pH

The reconstituted solution was used to measure pH. No significant changes in pH were observed in all the samples through the course of the study. The pH values of the formulations were in the range of 3.0 to 3.3.

UV Spectroscopy

The protein concentration was measured using the UV spectroscopy method. The UV spectrum could also provide information on protein aggregation (baseline light scattering). For protein concentrations from 0.01 to 0.1 mg/mL, a 10-mm cuvette was used. For protein concentrations from 2 to 9 mg/mL, a 1-mm cuvette was used with no dilution or no sample disrupted. No significant changes in protein concentrations were observed in the samples of 0.1 to 9 mg/mL through out the course of the stability study. For the low concentration samples of 0.01 and 0.03 mg/ml, more variation was seen because the absorbance was too low. A new sample preparation method should be needed for the low concentration samples for future studies.

Non-reduced rpHPLC Results

The non-reduced rpHPLC is used to monitor degraded species of rhGDF-5, such as methionine oxidation and deamidation. No significant changes in percentage of the main peak were observed in all the samples stored at 2-8° C., 25° C. and 40° C. through out 6-month storage. The main peak of rhGDF-5 of samples that were stored for 6-months was still recovered with ≧96% and it was comparable to the data obtained from time zero samples. The low concentration samples of 0.01 and 0.03 mg/mL were difficult to analyze by the HPLC method. A new sample preparation should be needed for future studies.

SEC

SEC was used to monitor protein aggregation. There were no significant changes found in aggregation of all the samples, which were tested throughout the 6-month stability study. The low concentration samples of 0.01 and 0.03 mg/mL were not analyzed.

Gel Electrophoresis

Protein aggregation and degradation species were also monitored using gel electrophoresis. There were no significant changes found in all the samples through out 6-month storage.

Small fragments of the protein were not formed in any sample during the storages, as these were not found on reduced SDS-PAGE Water Content The water contents of the samples were low, ranging from 0.19 to 0.32%. No correlation or trend was seen between the protein concentrations and water contents.

The results indicate that the lyophilized rhGDF-5 products in the presence of trehalose and glycine buffer are stable at 2-8° C., 25° C./60% RH and 40° C./75% RH for at least 6 months, as evidenced by rpHPLC and SEC chromatography. The protein can be formulated at various concentrations ranging from 0.1 to 9 mg/mL (pre-lyophilization) with 5% (w/v) trehalose/5 mM glycine-HCl buffer (pH 3) and lyophilized. When the protein was formulated at low concentration such as 0.01 mg/mL and 0.03 mg/mL, the existing methods have some limitations to detect the changes.

The present invention has been described relative to illustrative embodiments. Since certain changes may be made in the above formulations without departing from the scope of the invention, it is intended that all matter contained in the above description or shown in the accompanying drawings be interpreted as illustrative and not in a limiting sense. For example, one skilled in the art will recognize that the formulation of the illustrative embodiments of the invention is not limited to use with BMP and can be used with other biomolecules for any suitable biologic system.

It is also to be understood that the following claims are to cover all generic and specific features of the invention described herein, and all statements of the scope of the invention, which, as a matter of language, might be said to fall there between.

What is claimed is:

1. A method of treating a patient having a defect selected from the group consisting of a bone defect, a cartilage defect, a tendon defect, a ligament defect, and an intervertebral disc defect comprising the steps of:
   a. providing a composition comprising a biocompatible matrix, an rhGDF-5, a glycine, and an amount of trehalose sufficient to stabilize said rhGDF-5, wherein said composition has a pH of about 2.5 to about 3.5,
   b. adding a bone marrow aspirate to said composition, and
   c. implanting said biocompatible matrix into said defect.

2. The method of claim 1, wherein said biocompatible matrix is selected from the group consisting of collagen, mineralized collagen, salts of calcium phosphate, ceramics containing calcium, autogenic bone, allogenic bone, xenogenic bone, polylactide (PLA), polyglycolide (PGA), PLA-PGA co-polymers, polycarbonate, polycaprolactone, and mixtures thereof.

3. A method of treating a patient having a defect is selected from the group consisting of a bone defect, a cartilage defect, a tendon defect, a ligament defect, and an intervertebral disc defect comprising the steps of:
   a. providing a biocompatible matrix,
   b. providing a composition comprising, an rhGDF-5, a glycine, an amount of trehalose sufficient to stabilize said rhGDF-5, wherein said rhGDF-5 composition has a pH of about 2.5 to about 3.5,
   c. lyophilizing said rhGDF-5 composition,
   d. providing an amount of sterile water sufficient to reconstitute said lyophilized rhGDF-5 composition,
   e. adding said water to said lyophilized rhGDF-5 composition to reconstitute said rhGDF-5 composition into solution,
   f. applying said reconstituted rhGDF-5 solution to said biocompatible matrix, and
   g. implanting said biocompatible matrix into said patient.

4. The method of claim 3, further comprising the step of adding bone marrow aspirate to said biocompatible matrix.

5. The method of claim 3, wherein said biocompatible matrix is selected from the group consisting of collagen, mineralized collagen, salts of calcium phosphate, ceramics containing calcium, autogenic bone, allogenic bone, xenogenic bone, polylactide (PLA), polyglycolide (PGA), PLA-PGA co-polymers, polycarbonate, polycaprolactone, and mixtures thereof.

* * * * *